United States Patent
Haymore

(10) Patent No.: US 9,120,846 B2
(45) Date of Patent: Sep. 1, 2015

(54) NEUTRAL ZWITTERIONIC DISPLACER MOLECULES FOR HYDROPHOBIC DISPLACEMENT CHROMATOGRAPHY

(71) Applicant: SACHEM, INC., Austin, TX (US)

(72) Inventor: Barry L. Haymore, Austin, TX (US)

(73) Assignee: Sachem, Inc., Austin, TX (US)

( * ) Notice: Subject to any disclaimer, the term of this patent is extended or adjusted under 35 U.S.C. 154(b) by 0 days.

(21) Appl. No.: 14/349,102

(22) PCT Filed: Oct. 3, 2012

(86) PCT No.: PCT/US2012/000433
§ 371 (c)(1),
(2) Date: Apr. 2, 2014

(87) PCT Pub. No.: WO2013/052087
PCT Pub. Date: Apr. 11, 2013

(65) Prior Publication Data
US 2014/0256910 A1    Sep. 11, 2014

Related U.S. Application Data

(60) Provisional application No. 61/542,424, filed on Oct. 3, 2011.

(51) Int. Cl.
| | | |
|---|---|---|
| *A61K 38/00* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *C07K 1/20* | (2006.01) | |
| *B01D 15/32* | (2006.01) | |
| *B01D 15/42* | (2006.01) | |

(52) U.S. Cl.
CPC ........... *C07K 1/20* (2013.01); *B01D 15/325* (2013.01); *B01D 15/422* (2013.01)

(58) Field of Classification Search
CPC ...... C09K 8/602; B01D 15/30; B01D 15/325; B01D 15/362; B01D 15/363; B01D 15/3804; B01D 15/422; B01D 17/074
See application file for complete search history.

(56) References Cited

U.S. PATENT DOCUMENTS

| | | | |
|---|---|---|---|
| 6,239,262 B1 | 5/2001 | Cramer et al. | |
| 6,776,893 B1 * | 8/2004 | Too et al. | 205/123 |
| 2011/0166332 A1 | 7/2011 | Gagnon | |

OTHER PUBLICATIONS

GE Healthcare Life Sciences, Octyl Sepharose 4 Fast Flow, accessed online on Apr. 3, 2015 at http://www.gelifesciences.com/webapp/wcs/stores/servlet/productById/en/GELifeSciences-us/17094604.*
Khurram M. Sunasara et al.: "Application of hydrophobic interaction displacement chromatography for an industrial protein purification", Biotechnology and Bioengineering, vol. 82, No. 3, May 5, 2003, pp. 330-339.
PCT/US2012/000433; PCT International Search Report and Written Opinion of the International Searching Authority dated Dec. 4, 2012.

\* cited by examiner

*Primary Examiner* — Marcela M Cordero Garcia
*Assistant Examiner* — Kaipeen Yang
(74) *Attorney, Agent, or Firm* — Renner, Otto, Boisselle & Sklar, LLP

(57) ABSTRACT

A process for separating organic compounds from a mixture by reverse-phase displacement chromatography, including providing a hydrophobic stationary phase; applying to the hydrophobic stationary phase a mixture comprising organic compounds to be separated; displacing the organic compounds from the hydrophobic stationary phase by applying thereto an aqueous composition comprising a non-surface active hydrophobic neutral zwitterionic displacer molecule and optionally an organic solvent; and collecting a plurality of fractions eluted from the hydrophobic stationary phase containing the separated organic compounds; in which the non-surface active hydrophobic neutral zwitterionic displacer molecule comprises a hydrophobic zwitterion having the general formula, as defined in the disclosure: [CM-R*—CM'].

21 Claims, 1 Drawing Sheet

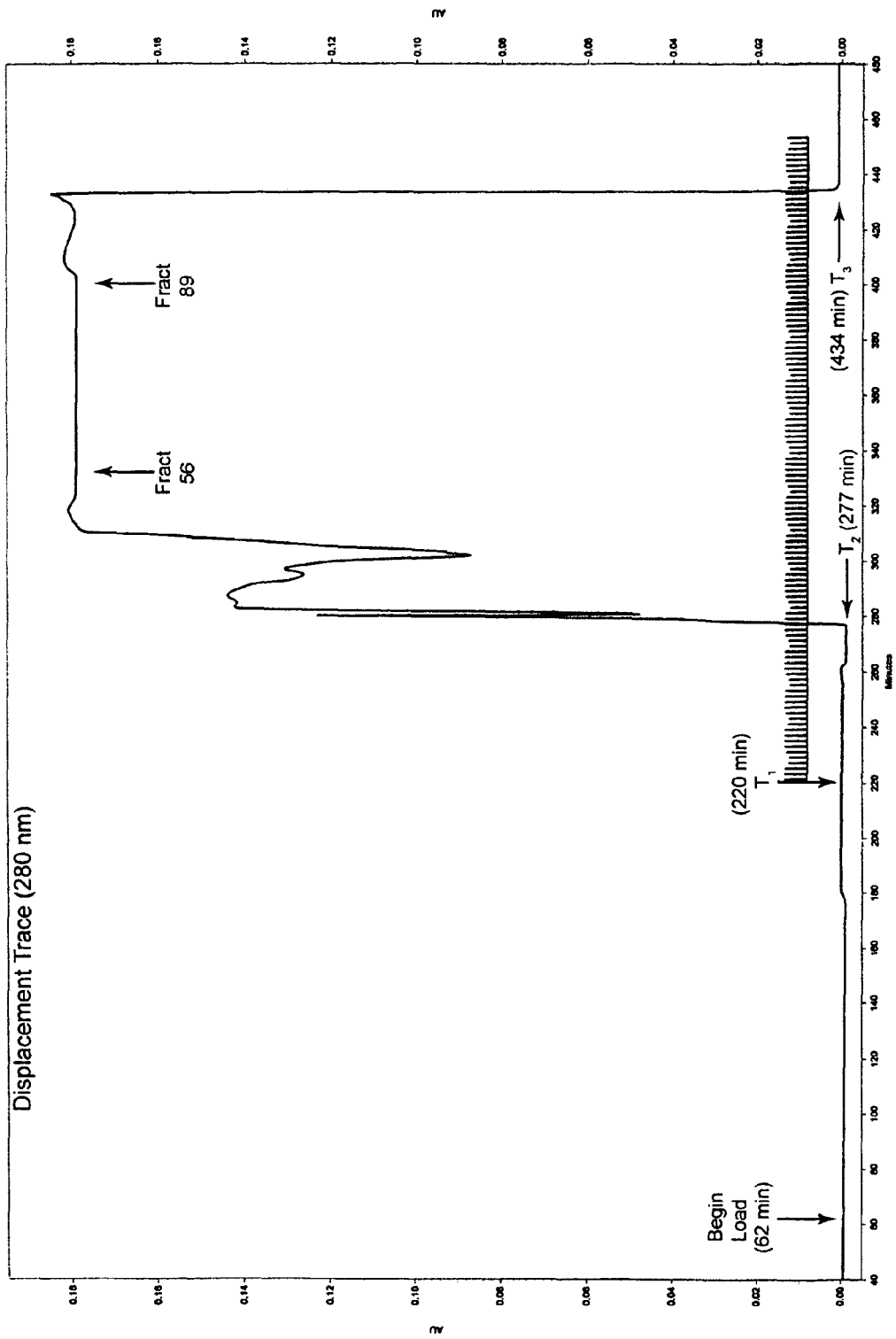

NEUTRAL ZWITTERIONIC DISPLACER MOLECULES FOR HYDROPHOBIC DISPLACEMENT CHROMATOGRAPHY

The present application is a U.S. National Stage Application based on and claiming benefit and priority under 35 U.S.C. §371 of International Application No. PCT/US2012/000433, filed Oct. 3, 2012, which in turn claims benefit of and priority to U.S. Application No. 61/542,424, filed Oct. 3, 2011, the entirety of each of which is hereby incorporated herein by reference.

BACKGROUND

Displacement chromatography (DC) in one of the three well-defined forms of column chromatography—elution, displacement, frontal. DC is principally a preparative method, but there are also analytical applications using "micro-preparative" DC with packed "narrow-bore" or capillary columns.

Displacement chromatography may be carried out using any one of four general chromatographic methods when suitable, high-purity displacer molecules are available. DC is used in (a) ion-exchange chromatography (cation-exchange, anion-exchange), (b) hydrophobic chromatography (reversed-phase, hydrophobic-interaction, hydrophobic charge-induction, thiophilic), (c) normal-phase chromatography including hydrophilic-interaction chromatography (HILIC) and (d) immobilized metal-ion affinity chromatography (IMAC).

With optimized DC, one may obtain, simultaneously, high purity (high resolution), high recovery (high yield) and high column loading (high capacity)—the latter much higher than overloaded preparative elution chromatography. In most cases, these advantages more than compensate for the disadvantages of DC (slower flow-rates, longer run-times, need for high-purity displacers).

Displacement chromatography is carried out by choosing (a) an applicable chromatographic method, (b) a suitable chromatography column with proper dimensions, (c) proper mobile phase conditions, (d) a suitable displacer molecule and (e) suitable operation protocols with properly configured LC equipment. Initially, a suitable "weakly displacing mobile phase" (carrier) is chosen, and the column is equilibrated at a suitable flow-rate. The carrier may contain a pH-buffering compound adjusted to a useful pH value. Optimal displacement flow-rates tend to be low, typically in the range of 35-105 cm/hr, though sometimes higher. A suitable amount of the sample solution is loaded onto the column at the sample-loading flow-rate. The sample solution contains the material to be purified in the carrier along with the proper level of an ion-pairing agent or ion-pairing salt if the sample or displacer molecules are charged or zwitterionic. Typical sample loadings are 50-80% of the operative breakthrough capacity. Next, a displacer mobile phase (displacer buffer), prepared from a suitable displacer compound at the proper concentration in the carrier solution, is pumped onto the column at the displacement flow-rate until the displacer breakthrough is observed. The purified sample comes off the column before the displacer breakthrough front. Fractions from the column are collected and separately analyzed for content and purity. Finally, the displacer is removed from column using a "displacer removal solution", and then the column is cleaned and regenerated to its original state for storage or for subsequent use.

Though different from elution chromatography, in some respects, displacement chromatography is easy to understand and easy to carry out. In DC, a sample is "displaced" from the column by the displacer, rather than "eluted" from the column by the mobile phase. When the output of the column is monitored online (e.g., via UV absorption, pH, or conductivity), a "displacement train" is obtained rather than an "elution chromatogram". The displacement train is composed of side-by-side "displacement bands" rather than solvent-separated "elution peaks" in a chromatogram. When a displacement band is large enough to saturate the stationary phase, a trapezoidal "saturating band" is formed. When a displacement band is not large enough to saturate the stationary phase, a small, triangular "non-saturating band" is formed. The height of a saturating band is determined by the binding isotherm at the point of operation; the area of a trapezoid-band or a triangle-band is proportional to the amount of the component.

Hydrophobic chromatography depends almost exclusively on the unique solvation properties of water that result from the highly structured, self-associated, hydrogen-bonded liquid. For conventional reversed-phase chromatography stationary phases (uncharged $C_{18}$ column), binding is usually driven by entropy ($+T\Delta S$), which often must overcome unfavorable enthalpy ($+\Delta H$). Thus, over the temperature ranges often used by chromatographers (10-70° C.), analyte-binding and displacer-binding often become stronger with increasing temperature. Another useful feature of hydrophobic chromatography is the use of additives that modify both the structure and strength of the self-hydrogen-bonding of the aqueous-based solvent. These additives include: salts (NaCl, $K_2HPO_4$, $(NH_4)_2SO_4$), organic solvents (MeCN, MeOH, EtOH) and polar organic molecules (urea, oligo-ethyleneglycol) in chromatography buffers.

Hydrophobic displacement chromatography can be carried out using chiral analytes, chiral displacers and chiral chromatography matrices. Under these conditions, an achiral displacer may be used, but a racemic mixture of a chiral displacer cannot be used. Racemic chiral analytes can also be purified using an achiral chromatography column and an achiral displacer. In this case, impurities, including diastereomers, are removed from the racemic compound of interest, but there is no chiral resolution of the enantiomers. Development of useful, preparative hydrophobic displacement chromatography has been hampered by the unavailability of suitable, high-purity displacer molecules. We describe here new displacer molecules and methods to use them that have utility in various forms of hydrophobic displacement chromatography.

Good hydrophobic displacer molecules should possess a unique combination of chemical and physical properties in order for them to function efficiently. Some soluble, hydrophobic molecules can function as displacers, but only a limited few function well. Many of the molecules described in this document fulfill the necessary requirements for well-functioning displacers.

Development of useful, reversed phase, preparative displacement chromatography has been hampered by the unavailability of suitable, high-purity displacer molecules. For example, U.S. Pat. No. 6,239,262 describes various reversed phase liquid chromatographic systems using low molecular weight surface-active compounds as displacers. U.S. Pat. No. 6,239,262 discloses an extremely wide range of possible charged moieties that may be coupled with hydrophobic moieties to form the disclosed surface active compounds used as displacers, but discloses that it is necessary to include a large proportion of organic solvent to mitigate the surface active properties of the disclosed displacers. The presence of such large proportions of organic solvents significantly alters the process, derogating from the benefits of reverse-phase hydrophobic displacement chromatography. In addition, the strongly surface-active displacer compounds disclosed by U.S. Pat. No. 6,239,262 do not function well, resulting in relatively poor-to-mediocre quality displacement trains in which a significant level of impurities may be present in the "purified" products.

SUMMARY

We have discovered and developed classes of neutral hydrophobic zwitterionic or dizwitterionic compounds, that uniquely possess that combination of chemical and physical properties necessary for good displacer behavior in hydrophobic displacement chromatography.

Accordingly, the present invention, in one embodiment, relates to a process for separating organic compounds from a mixture by reverse-phase displacement chromatography, comprising:

providing a hydrophobic stationary phase;

applying to the hydrophobic stationary phase a mixture comprising organic compounds to be separated;

displacing the organic compounds from the hydrophobic stationary phase by applying thereto an aqueous composition comprising a non-surface-active hydrophobic neutral zwitterionic displacer molecule; and collecting a plurality of fractions eluted from the hydrophobic stationary phase containing the separated compounds;

wherein the non-surface active hydrophobic neutral zwitterionic displacer molecule comprises a hydrophobic neutral zwitterionic molecule, having the general formula:

[CM-R*—CM']

wherein in the general formula, CM is an independent hydrophobic chemical moiety with a formal positive (+) charge selected from: quaternary ammonium (I), quaternary phosphonium (II), sulfonium (III), sulfoxonium (IV), imidazolinium (amidinium) (V), guanidinium (VI), imidazolium (VII), 1,2,3,4-tetrahydroisoquinolinium (VIII), 1,2,3,4-tetrahydroquinolinium (IX), isoindolinium (X), indolinium (XI), benzimidazolium (XII), pyridinium (XIIIa, XIIIb, XIIIc, XIIId), quinolinium (XIV), isoquinolinium (XV), and CM' is an independent hydrophobic chemical moiety with a formal negative (−) charge selected from: carboxylate (XVI), N-acyl-α-amino acid (XVII), sulfonate (XVIII), sulfate monoester (XIX), phosphate monoester (XX), phosphate diester (XXI), phosphonate monoester (XXII), phosphonate (XXIII), tetraaryl borate (XXIV), boronate (XXV), boronate ester (XXVI); wherein the chemical moieties (I)-(XXVI) have the following chemical structures:

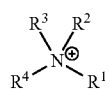

I

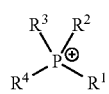

II

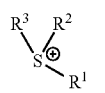

III

IV

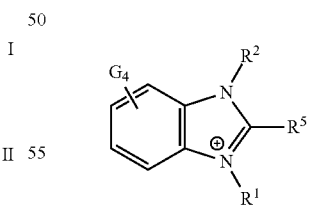

V

VI

VII

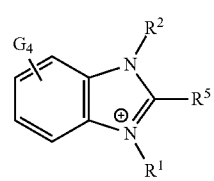

VIII

IX

X

XI

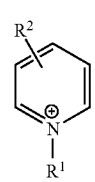

XII

XIIIa

-continued

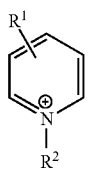

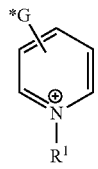

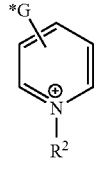

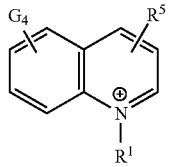

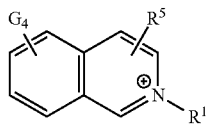

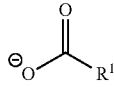

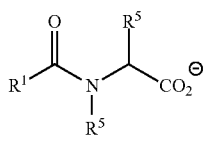

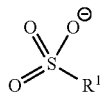

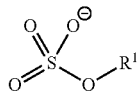

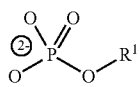

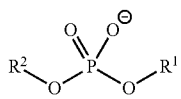

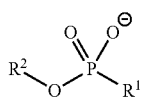

-continued

XIIIb
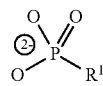

XIIIc
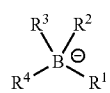

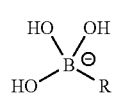

XIIId

XIV

XV

XVI

XVII

XVIII

XIX

XX

XXI

XXII

XXIII

XXIV

XXV

XXVI wherein in the general formula, CM and CM' are independent charged chemical moieties having the opposite formal charge such that the molecule as a whole is an electrically neutral zwitterion having zero formal charge at operational pH and CM and CM' are chemically attached to each other by a doubly connected chemical moiety, R*, which replaces one $R^1$, $R^2$ (if present), $R^3$ (if present) or $R^4$ (if present) chemical moiety on CM and replaces one $R^{1'}$, $R^{2'}$ (if present), $R^{3'}$ (if present) or $R^{4'}$ (if present) chemical moiety on CM' (herein, an R group on CM' is designated with a prime ('), e.g., $R^{1'}$ is the $R^1$ group on CM');

wherein each of $R^1$, $R^{1'}$, $R^2$, $R^{2'}$, $R^3$, $R^{3'}$, $R^4$ and $R^{4'}$ is a linear or branched chemical moiety independently defined by the formula, $$-C_xX_{2x-2r}\text{-}AR^1-C_uX_{2u-2s}\text{-}AR^2,$$

R* is a direct chemical bond or is a doubly connected, linear or branched chemical moiety connecting CM to CM' defined by the formula, $$-C_xX_{2x-2r}\text{-}AR^1-C_uX_{2u-2s}-,$$

and $R^5$ and $R^{5'}$ independently are a linear or branched chemical moiety defined by the formula, $$-C_xX_{2x-2r}\text{-}AR^2;$$

wherein each $AR^1$ independently is a doubly connected methylene moiety ($-CX^1X^2-$, from methane), a doubly connected phenylene moiety ($-C_6G_4$-, from benzene), a doubly connected naphthylene moiety ($-C_{10}G_6$-, from naphthalene) or a doubly connected biphenylene moiety ($-C_{12}G_8$-, from biphenyl);

wherein $AR^2$ independently is hydrogen ($-H$), fluorine ($-F$), a phenyl group ($-C_6G_5$), a naphthyl group ($-C_{10}G_7$) or a biphenyl group ($-C_{12}G_9$);

wherein each X, $X^1$ and $X^2$ is individually and independently $-H$, $-F$, $-Cl$ or $-OH$;

wherein any methylene moiety ($-CX^1X^2-$) within any $-C_xX_{2x-2r}-$ or within any $-C_uX_{2u-2s}-$ or within any $-(CX^1X^2)_p-$ may be individually and independently replaced with an independent ether-oxygen atom, $-O-$, an independent thioether-sulfur atom, $-S-$, or an independent ketone-carbonyl group, $-C(O)-$, in such a manner that each ether-oxygen atom, each thioether-sulfur atom or each ketone-carbonyl group is bonded on each side to an aliphatic carbon atom or an aromatic carbon atom;

wherein not more than two ether-oxygen atoms, not more than two thioether-sulfur atoms and not more than two ketone-carbonyl groups may be replaced into any —$C_xX_{2x-2r}$— or into any —$C_uX_{2u-2s}$—;

wherein $m_x$ is the total number of methylene groups in each —$C_xX_{2x-2r}$— that are replaced with ether-oxygen atoms, thioether-sulfur atoms and ketone-carbonyl groups, and $m_u$ is the total number of methylene groups in each —$C_uX_{2u-2s}$— that are replaced with ether-oxygen atoms, thioether-sulfur atoms and ketone-carbonyl groups;

wherein G is individually and independently any combination of —H, —F, —Cl, —$CH_3$, —OH, —$OCH_3$, —$N(CH_3)_2$, —$CF_3$, —$CO_2Me$, —$CO_2NH_2$; —$CO_2NHMe$, —$CO_2NMe_2$;

wherein G* is individually and independently any combination of —F, —Cl, —$R^2$, —OH, —$OR^2$, —$NR^2R^3$, —$CF_3$, —$CO_2Me$, —$CO_2NH_2$; —$CO_2NHMe$, —$CO_2NMe_2$;

wherein a pair of $R^2$, $R^{2'}$, $R^3$, $R^{3'}$, $R^4$ and $R^{4'}$ may comprise a single chemical moiety such that $R^2/R^3$, $R^2/R^4$, $R^3/R^4$, $R^{2'}/R^{3'}$, $R^{2'}/R^{4'}$ or $R^{3'}/R^{4'}$ is individually and independently —$(CX^1X^2)_p$— with p=3, 4, 5 or 6;

wherein the integer values of each of x, r, u, s, $m_x$, $m_u$ are independently selected for each $R^1$, $R^{1'}$, $R^2$, $R^{2'}$, $R^3$, $R^{3'}$, $R^4$, $R^{4'}$, $R^5$, $R^{5'}$ and R*, integer values r and s are the total number of contained, isolated cis/trans olefinic (alkene) groups plus the total number of contained simple monocyclic structures and fall in the ranges 0≤r≤2 and 0≤s≤2, the numeric quantity x+u−$m_x$−$m_u$ falls in the range 0≤x+u−$m_x$−$m_u$≤11;

wherein at least one aromatic chemical moiety, heterocyclic aromatic chemical moiety, imidazoline chemical moiety, amidine chemical moiety or guanidine chemical moiety is contained within CM or CM';

wherein a group-hydrophobic-index for each R-chemical-moiety (n) is numerically equal to the sum of the number of aliphatic carbon atoms plus the number of olefinic carbon atoms plus the number of thioether-sulfur atoms plus the number of chlorine atoms plus one-fifth the number of fluorine atoms plus one-half the number of ether-oxygen atoms plus one-half the number of ketone-carbon atoms plus one-half the number of aromatic carbon atoms beyond the number six minus the number of hydroxyl-oxygen atoms beyond the number one;

wherein an overall-hydrophobic-index (N) for each [CM-R*—CM'] is numerically equal to the sum of the number of aliphatic carbon atoms plus the number of olefinic carbon atoms plus the number of thioether-sulfur atoms plus the number of chlorine atoms plus one-fifth the number of fluorine atoms plus one-half the number of ether-oxygen atoms plus one-half the number of ketone-carbon atoms plus one-half the number of aromatic carbon atoms beyond the number six minus the number of hydroxyl-oxygen atoms beyond the number one;

wherein each of the group-hydrophobic-indices ($^1$n and $^{1'}$n) for $R^1$ and $R^{1'}$ fall in the range 4.0<$^1$n, $^{1'}$n<12.0, each of the group-hydrophobic-indices ($^2$n, $^{2'}$n, $^3$n, $^{3'}$n, $^5$n, $^{5'}$n and *n) for $R^2$, $R^{2'}$, $R^3$, $R^{3'}$, $R^5$, $R^{5'}$, R*, when present, fall in the range 0.0≤$^2$n, $^{2'}$n, $^3$n, $^{3'}$n $^5$n, $^{5'}$n, *n<12.0 and each of the group-hydrophobic-indices ($^4$n and $^{4'}$n) for $R^4$ and $R^{4'}$, when present, fall in the range 0.0≤$^4$n, $^{4'}$n≤5.0;

wherein the overall-hydrophobic-index (N) falls in the range 10.0≤N<24.0;

wherein the numeric value of the group-hydrophobic-index calculated for a cyclic chemical moiety is divided equally between the two respective R-chemical-moieties;

wherein $R^1$ is identified as that R-chemical-moiety when only one such chemical moiety is attached to CM or CM'; wherein $R^1$ is identified as that R-chemical-moiety having the largest value of the group-hydrophobic-index when there are more than one such R-chemical-moieties attached to CM or CM'; wherein $R^4$ is identified as that R-chemical-moiety having the smallest value of the group-hydrophobic-index when there are more than three such chemical moieties attached to CM or CM'.

In general herein, CM is a cation and CM' is an anion, and each of CM and CM' can include more than one cation or anion, respectively, so long as electrical neutrality in [CM-R*—CM'] is maintained.

In one embodiment, the aqueous composition comprising a non-surface active hydrophobic displacer molecule is free of added salt other than a pH buffer.

In one embodiment, CM has a general formula I or II:

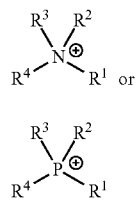

wherein in the general formula I or II, $R^1$ is a $C_8$-$C_{11}$ hydrocarbyl moiety, $R^2$ and $R^3$ are independently a $C_1$-$C_4$ hydrocarbyl moiety or benzyl, and $R^4$ is selected from benzyl, halo-substituted benzyl, 4-alkylbenzyl, 4-trifluoromethyl benzyl, 4-phenylbenzyl, 4-alkoxybenzyl, 4-acetamidobenzyl, $H_2NC(O)CH_2$—, PhHNC(O)$CH_2$—, dialkyl-NC(O)$CH_2$—, wherein alkyl is $C_1$-$C_4$, provided that no more than one benzyl group is present in the CM.

In one embodiment, CM has a general formula I or II:

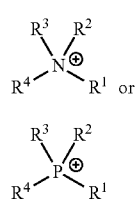

wherein in the general formula I or II, $R^1$ and $R^2$ are independently $C_4$-$C_8$ alkyl or cyclohexyl, $R^3$ is $C_1$-$C_4$ alkyl, and $R^4$ is phenyl, 2-, 3- or 4-halophenyl, benzyl, 2-, 3- or 4-halobenzyl, 2,3-, 2,4-, 2,5-, 2,6-, 3,4- or 3,5-dihalobenzyl, 2,4,6- or 3,4,5-trihalobenzyl, $C_6H_5CH_2CH_2$— or 2-, 3- or 4-trifluoromethylbenzyl.

In one embodiment, CM has a general formula VIII, IX, X or XI, $R^1$ is $C_5$-$C_{11}$ alkyl and $R^2$ is $C_1$-$C_8$ alkyl and G is as defined above.

In one embodiment, CM has a general formula I or II:

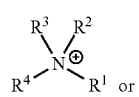

-continued

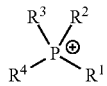
II wherein in the general formula I or II, $R^1$ is $C_6$-$C_{11}$ alkyl, $R^2$ and $R^3$ independently are $C_1$-$C_4$ alkyl, and $R^4$ is PhC(O)CH$_2$—, 4—FC$_6$H$_4$C(O)CH$_2$—, 4—CH$_3$C$_6$H$_4$C(O)CH$_2$—, 4-CF$_3$C$_6$H$_4$C(O)CH$_2$—, 4-ClC$_6$H$_4$C(O)CH$_2$-4-BrC$_6$H$_4$C(O)CH$_2$—, dl-PhC(O)CH(Ph)-, Ph(CH$_2$)$_2$—, Ph(CH$_2$)$_3$—, Ph(CH$_2$)$_4$—, dl-PhCH$_2$CH(OH)CH$_2$—, t-PhCH=CHCH$_2$—, 1-(CH$_2$)naphthylene, 9-(CH$_2$)anthracene, 2-, 3- or 4-F C$_6$H$_4$CH$_2$— or benzyl.

In one embodiment, CM has a general formula I or II:

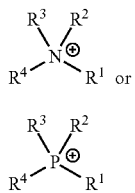

I

II $R^1$ is $C_6$-$C_{11}$ alkyl, $R^2$ and $R^3$ together are —(CH$_2$)$_4$—, and $R^4$ is PhC(O)CH$_2$—, 4—FC$_6$H$_4$C(O)CH$_2$—, 4-CH$_3$C$_6$H$_4$C(O)CH$_2$—, 4-CF$_3$C$_6$H$_4$C(O)CH$_2$-4-ClC$_6$H$_4$C(O)CH$_2$—, 4-BrC$_6$H$_4$C(O)CH$_2$—, dl-PhC(O)CH(Ph)-, Ph(CH$_2$)$_2$—, Ph(CH$_2$)$_3$—, Ph(CH$_2$)$_4$—, dl-PhCH$_2$CH(OH)CH$_2$—, t-PhCH=CHCH$_2$—, 2-, 3- or 4-FC$_6$H$_4$CH$_2$—, benzyl, 3-ClC$_6$H$_4$CH$_2$—, 2,6-F$_2$C$_6$H$_3$CH$_2$—, F$_2$C$_6$H$_3$CH$_2$—, 4-CH$_3$C$_6$H$_4$CH$_2$—, 4-CH$_3$CH$_2$C$_6$H$_4$CH$_2$—, 4-CH$_3$OC$_6$H$_4$CH$_2$—, (CH$_3$)$_2$NC(O)CH$_2$— or (CH$_3$CH$_2$)$_2$NC(O)CH$_2$—.

In one embodiment, CM has a general formula I or II:

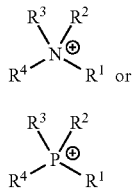

I

II wherein in the general formula I or II, $R^1$ is $C_4$-$C_6$ alkyl, benzyl or 2-, 3- or 4-FC$_6$H$_4$CH$_2$—, $R^2$ and $R^3$ independently are $C_1$-$C_8$ alkyl, CH$_3$(OCH$_2$CH$_2$)$_2$—, CH$_3$CH$_2$OCH$_2$CH$_2$OCH$_2$CH$_2$— or CH$_3$CH$_2$OCH$_2$CH$_2$—, and $R^4$ is Ph(CH$_2$)$_4$—, 4-PhC$_6$H$_4$CH$_2$—, 4-FC$_6$H$_4$CH$_2$—, 4-CF$_3$C$_6$H$_4$CH$_2$—, PhC(O)CH$_2$—, 4-FC$_6$H$_4$C(O)CH$_2$—, 4-PhC$_6$H$_4$C(O)CH$_2$—, 4-PhC$_6$H$_4$CH$_2$—, naphthylene-1-CH$_2$—, anthracene-9-CH$_2$— or Ph(CH$_2$)$_n$—, where n=5-8.

In one embodiment, CM has a general formula [(R$^1$R$^2$R$^3$NCH$_2$)$_2$C$_6$H$_3$G]$^{2+}$, wherein $R^1$ is $C_4$-$C_{11}$ alkyl, $R^2$ and $R^3$ independently are $C_1$-$C_6$ alkyl or $R^2$ and $R^3$ taken together are —(CH$_2$)$_4$—, and G is H or F.

In one embodiment, CM has a general formula [R$^1$R$^2$R$^3$NCH$_2$C$_6$H$_4$—C$_6$H$_4$CH$_2$NR$^1$R$^2$R$^3$]$^{2+}$, wherein $R^1$ is $C_4$-$C_{11}$ alkyl, $R^2$ and $R^3$ independently are $C_1$-$C_6$ alkyl or $R^2$ and $R^3$ taken together are —(CH$_2$)$_4$—.

In one embodiment, CM has a general formula III or IV:

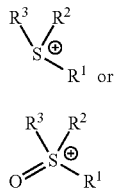

III

IV wherein in the general formula III or IV, $R^1$ is $C_8$-$C_{11}$ alkyl or 4,4'-CH$_3$(CH$_2$)$_4$C$_6$H$_4$—C$_6$H$_4$CH$_2$—, $R^2$ is $C_1$-$C_6$ alkyl or 4-FC$_6$H$_4$CH$_2$—, and $R^3$ is $C_1$-$C_6$ alkyl.

In one embodiment, CM has a general formula XIV or XV:

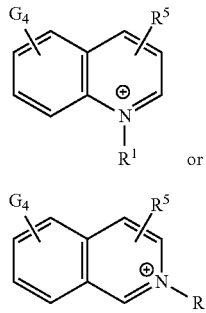

XIV

XV wherein in the general formula XIV or XV, $R^1$ is $C_8$-$C_{11}$ alkyl, and each G and $R^5$ are as defined above.

In one embodiment, CM has a general formula XIIIa, XIIIb, XIIIc, XIIId or XIIIe:

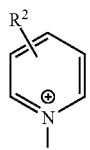

XIIIa

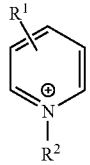

XIIIb

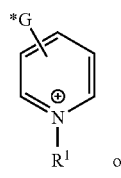

XIIIc

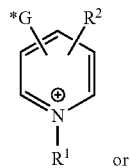

XIIId

-continued

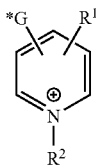

XIIIe wherein in the general formula XIIIa, XIIIb, XIIIc, XIIId or XIIIe, $R^1$ is $C_8$-$C_{11}$ alkyl or $C_8$-$C_{11}$ 4-phenyl, $R^2$ is H, $C_1$-$C_6$ alkyl or alkoxy, 2-pyridyl, $C_1$-$C_6$ alkyl substituted 2-pyridyl, or pyrrolidinyl, and each G is as defined above.

In one embodiment, CM has a general formula VII:

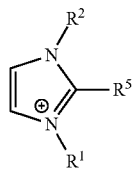

VII wherein in the general formula VII, $R^1$ is $C_6$-$C_{11}$ alkyl, $R^2$ and $R^5$ are independently H or $C_1$-$C_6$ alkyl or phenyl.

In one embodiment, CM has a general formula XII:

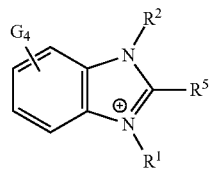

XII wherein in the general formula XII, $R^1$ is $C_5$-$C_{11}$ alkyl, $R^2$ and $R^5$ are independently H or $C_1$-$C_6$ alkyl or phenyl, and G is as defined above.

In one embodiment, CM,\' has a general formula XXIV or XXV:

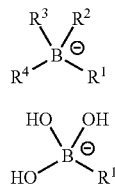

XXIV

XXV wherein in the general formula XXIV, $R^1$ is phenyl, 4-EtC$_6$H$_4$—, 4-"PrC$_6$H$_4$—, 4-"BuC$_6$H$_4$—, 4-MeOC$_6$H$_4$—, 4-FC$_6$H$_4$—, 4-MeC$_6$H$_4$—, 4-MeOC$_6$H$_4$—, 4-EtC$_6$H$_4$—, 4-ClC$_6$H$_4$—, or C$_6$F$_5$—; and each of $R^2$, $R^3$ and $R^4$ independently are phenyl, 4-FC$_6$H$_4$—, 4-MeC$_6$H$_4$—, 4-MeOC$_6$H$_4$—, 4-EtC$_6$H$_4$—, 4-ClC$_6$H$_4$— or C$_6$F$_5$—; and wherein in the general formula XXV, $R^1$ is 4-(4-"BuC$_6$H$_4$)C$_6$H$_4$— or 4-(4-"BuC$_6$H$_4$)-3-ClC$_6$H$_3$—

In one embodiment, CM' has a general formula selected from 4-R$^1$C$_6$H$_4$SO$_3$H, 5-R$^1$-2-HO— C$_6$H$_3$SO$_3$H, 4-R$^1$—C$_6$H$_4$—C$_6$H$_3$X-4'-SO$_3$H, and 4-R$^1$—C$_6$H$_4$—C$_6$H$_3$X-3'-SO$_3$H, wherein R1 is CH$_3$(CH$_2$)$_n$, wherein n=4-10 and X is H or OH.

In one embodiment, CM' has a general formula XVIII or XXIII:

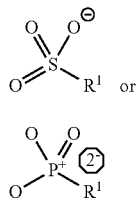

XVIII

XXIII wherein in the general formula XVIII and in the general formula XXIII, $R^1$ is $C_6H_5(CH_2)_n$—, wherein n=5-11.

In one embodiment, CM' has a general formula selected from 5-R$^1$-2-HO—C$_6$H$_3$CO$_2$H and R$^1$C(O)NHCH(C$_6$H$_5$)CO$_2$H, wherein $R^1$ is CH$_3$(CH$_2$)$_n$—, wherein n=4-10.

In one embodiment, CM' has a general formula 4-R$^1$C$_6$H$_4$PO$_3$H$_2$ wherein $R^1$ is CH$_3$(CH$_2$)$_n$—, wherein n=4-10.

In one embodiment, the aqueous composition further includes an organic solvent, in an amount of less than about 25% by volume, or less than about 20% by volume, or less than about 15% by volume, or less than about 10% by volume, or less than about 5% by volume.

BRIEF DESCRIPTION OF THE DRAWING

FIG. 1A is a displacement trace for the purification of a crude synthetic peptide plotting time (x-axis) against relative absorbance units (y-axis) for the displacement chromatography process in accordance with an exemplary embodiment of the present invention.

DETAILED DESCRIPTION

As used herein, "non-surface-active", with respect to a neutral zwitterionic non-surface-active displacer compound employed in accordance with the present invention, means that the compound so described has a critical micelle concentration ("CMC") greater than the concentration of the compound employed in a displacement chromatography process in accordance with the present invention. In one embodiment, the concentration of the non-surface-active displacer compound is less than about 80% of the CMC for that compound in water in the absence of organic solvent, salt or other agent that would affect the CMC. In one embodiment, the concentration of the non-surface-active displacer compound is less than about 60% of the CMC for that compound in water in the absence of organic solvent, salt or other agent that would affect the CMC. In one embodiment, the concentration of the non-surface-active displacer compound is less than about 50% of the CMC for that compound in water in the absence of organic solvent, salt or other agent that would affect the CMC.

In one embodiment, the aqueous composition comprising a non-surface active hydrophobic neutral zwitterionic displacer molecule employed in accordance with the present invention does not exhibit adverse surface-active characteristics due to one or a combination of two or more of (1) the zwitterionic non-surface active displacer compound is present at a concentration lower than its CMC; (2) the overall-hydrophobic-index (N) for each [CM-R*—CM'] falls in the range 10≤N<24; (3) the group-hydrophobic-index ($^1$n) for each $R^1$ or $R^{1'}$ falls in the range 4<$^1$n<12, the group-hydrophobic-index ($^2$n, $^3$n, $^5$n and *n) for each $R^2$, $R^{2'}$, $R^3$, $R^{3'}$, $R^5$, $R^{5'}$ and $R^*$, when present, falls in the range $0 \leq {}^2n$, ${}^3n$, ${}^6n, {}^*n < 12$, and the group-hydrophobic-index (${}^4n$) for each $R^4$ or $R^{4'}$, when present, falls in the range $0 \leq {}^4n \leq 5$; (4) the composition contains greater than about 5 volume % or more of an organic solvent; (5) the composition contains less that 0.1 M salt or greater than 1.0 M salt other than pH buffer needed to adjust and control the pH of the composition.

As used herein, "low organic solvent content" generally refers to an organic solvent content in, e.g., an aqueous "carrier" composition comprising a neutral zwitterionic non-surface-active displacer compound in accordance with the present invention, of less than about 25% by volume. In one embodiment, the organic solvent content of the aqueous "carrier" composition contains less than about 20% by volume of any organic solvent. In one embodiment, the organic solvent content of the aqueous "carrier" composition contains less than about 15% by volume of any organic solvent. In one embodiment, the organic solvent content of the aqueous "carrier" composition contains less than about 10% by volume of any organic solvent. In one embodiment, the organic solvent content of the aqueous "carrier" composition contains less than about 5% by volume of any organic solvent. In one embodiment, the aqueous "carrier" composition contains contains no organic solvent.

In one embodiment, the organic solvent is one or a mixture of two or more of methanol ($CH_3OH$ or MeOH), ethanol ($C_2H_5OH$ or EtOH) or acetonitrile ($CH_3CN$ or MeCN). In one embodiment, the aqueous "carrier" composition contains a mixture of suitable organic solvents. In one embodiment, the aqueous "carrier" composition contains no organic solvent.

Hydrophobic displacement chromatography can be carried out using chiral analytes, chiral displacers and chiral chromatography matrices. Under these conditions, an achiral displacer may be used, but a racemic mixture of a chiral displacer cannot be used. Racemic chiral analytes can also be purified using an achiral chromatography column and an achiral displacer. In this case, impurities, including diastereomers, are removed from the racemic compound of interest, but there is no chiral resolution of the enantiomers.

Some of the neutral zwitterionic displacers described here have a quaternary nitrogen with four different groups attached and hence are inherently chiral; see for example racemic displacer compounds 722, 736, 755 in Table V below. Furthermore, some of the neutral zwitterinic displacers contain a single chiral group attached to an achiral nitrogen atom; see for example displacer compound 731. With the proper choice of chiral chromatography matrix, mobile phase and achiral displacer, enantiomers are routinely preparatively resolved (separated). Depending on the specific circumstances, a good, enantiomerically pure, chiral displacer can have performance advantages over a good achiral displacer when carrying out a displacement separation of enantiomers on a chiral stationary phase.

Useful pH Ranges—

Various classes of neutral zwitterionic hydrophobic displacers having the general formula A or B, have different useful pH ranges depending on the chemical nature of the charged moieties. Neutral zwitterionic hydrophobic displacers that contain deprotonatable cationic groups should be operated at a pH of 1-2 units or more below the actual pKa values. Neutral zwitterionic hydrophobic displacers that contain protonatable anionic groups should be operated at a pH of 1-2 units or more above the actual pKa values.

Onium Groups—Generally, quaternary ammonium, quaternary phosphonium, tertiary sulfonium, tertiary sulfoxonium and related cationic groups such as pyridinium, imidazolium, guanidinium have a wide useful pH range, 1-11 or greater, because these groups do not have deprotonatable N—H, S—H or P—H moieties under normal conditions.

Amine and Guanidine Groups—Tertiary aliphatic amines (pKa~9.5) and related substituted quanidines (pKa~13.5) with deprotonatable N—H moieties are useful cationic groups when operated at a pH of 1-2 units or more below the actual pKa values.

Sulfonate Groups—Generally, aliphatic sulfonates (pKa~−2.0) and aromatic sulfonates (pKa~−2.5) have a wide useful pH range, 1-11, owing their very low pKa values.

Carboxylate Groups—Generally, simple aliphatic carboxylates (pKa~3.0-5.0), aromatic carboxylates (pKa~2.5-4.5), glycine derivatives including betaines (pKa~2.0) and β-alanine derivatives including homobetaines (pKa~3.5) are useful anionic moieties when operated at a pH of 1-2 units or more above the actual pKa values.

Phosphonate Groups—Phosphonates can be useful anionic groups, but their use is complicated by the second acid dissociation ($pK_{a2}$). Neutral zwitterionic hydrophobic displacers that contain a phosphonate group should be operated at a pH of 1-2 units or more above the actual $pK_{a1}$ and simultaneously 1-2 pH units below the actual $pK_{a2}$. Similarly, the displacer containing a phosphonate group should be operated at a pH of 1-2 units or more above the actual $pK_{a2}$ in order to obtain good chromatographic behavior. Generally, simple aliphatic phosphonates have $pK_{a1}$ and $pK_{a2}$ values of ~2.2 and 7.7, respectively, and simple aromatic phosphonates have $pK_{a1}$ and $pK_{a2}$ values of ~2.0 and 7.2, respectively.

Displacer Binding Strength—

The displacer should bind to the column more strongly than all of the components of the sample or at least more strongly than all of the major components of interest. A good rule-of-thumb is that no more than 1-4% of the sample mass should bind more strongly than the displacer.

An optimal displacer should bind to the stationary phase neither too strongly nor too weakly. The proper binding strength depends on the analyte of interest and the associated binding isotherms. Usually, a range of displacers with a range of binding strengths is needed for a variety of different columns and analytes to be purified. If a displacer binds too strongly, poor performance is obtained such as lower resolution, lower analyte binding capacity, difficulty in displacer removal and longer cycle times. If a displacer binds too weakly, a poor displacement train may result with too much "tailing" of the displaced analytes underneath the displacer, or there may be only partial displacement or no displacement at all.

A convenient, rule-of-thumb method that helps in choosing displacers with the proper binding strength is to carry out simple gradient elution chromatography of potential displacers and analytes using columns and mobile phases similar to those that are to be used in the displacement experiment. As a first screen, the displacer should elute 5-15 minutes later than the analytes of interest in a 60 minute gradient. Ideally one would measure the isotherms of the single analytes and mixtures of analytes but this is time-consuming and often impractical. Because it operates early on the binding isotherm, this rule-of-thumb method is not perfect, but provides a convenient starting point for further DC optimization.

Usable Binding Isotherms—

Apart from proper binding strength, useful hydrophobic displacers should have binding isotherms with certain other useful characteristics.

(1) Monomodal, convex upward isotherms (Langmuir-type isotherm behavior) for displacer and analyte molecules facilitate the orderly formation of isotactic displacement trains and simplify the method optimization process. This is a useful property of many neutral zwitterionic displacer molecules in contrast to binding isotherms of many other uncharged hydrophobic displacer molecules (non-zwitterions) such as aromatic alcohols (e.g., substituted phenols, naphthols, hydroxybiphenyls), fatty alcohols (e.g., 1-dodecanol, 1,2-dodecanediol) and uncharged fatty carboxylic acids (e.g., myristic acid) behave normally at lower concentrations and then become bimodal and rise again at higher concentrations (BET-type isotherm behavior). This binding behavior often arises from deposition of multiple layers of the hydrophobic displacer, each layer having different binding characteristics. This binding behavior greatly complicates the displacement process and its useful implementation.

(2) Chromatographic results in DC may be complicated when displacer molecules undergo self-association in solution. As concentrations increase, problems with displacer self-association become worse. Again, the charged groups in neutral zwitterionic hydrophobic displacers decrease or prevent self-association problems in aqueous solution.

(3) Further complications may arise when product and/or impurity isotherms cross the displacer isotherm in the higher, non-linear binding region. This behavior leads to reversal of displacement order, broadening of overlap regions between displacement bands and problems with co-displacement. In such case, minor variations in displacer concentration can lead to large changes in the displacement train thereby making method optimization very difficult.

We have found that properly designed hydrophobic neutral zwitterionic displacer molecules supplemented with the proper counter-ions and small amounts of selected organic solvents provide a family of effective hydrophobic neutral zwitterionic displacers with Langmuir-type binding behavior and useful ranges of binding strengths.

Ion-Pairing Agents—

With all of their many advantages, hydrophobic displacer molecules should have both a good ion-pairing agent for the analyte and a good ion-pairing salt for the neutral zwitterionic hydrophobic displacer. Ion-pairing anion is a salt which has a stronger ion-pairing anion and a weaker ion-pairing cation. Ion-pairing cation is a salt which has a weaker ion-pairing anion and a stronger ion-pairing cation. Ion-pairing salt is a salt in which both anion and cation have stronger ion-pairing properties. In practice, if both anion and cation have ion-pairing properties that are too strong, it won't dissolve very well in water. Ion-pairing salts have little relevance for the present invention except for neutral zwitterionic displacers and zwitterionic analytes that are near their pI. pI is the "isoelectric point", which is the pH or range of pH values of any zwitterionic chemical compound (often protein or peptide) at which the number of positive charges equals the number of negative charges, and the overall zwitterionic compound has a net zero charge.

The ion-pairing agent significantly affects the binding isotherm of the displacer and the functioning and utility of the displacer. The concentration of the ion-pairing agent is independently adjusted by adding appropriate amounts of $K^+$, $NH_4^+$, protonated amine salts of an ion-pairing anion or $Cl^-$/$HCO_2^-$ salts of an ion-pairing cation. The properties of an ion-pairing counter-ion for a charged hydrophobic displacer strongly affects its displacement properties. This is also true, but to a lesser extent, for neutral zwitterionic hydrophobic displacers. A few counter-ions may be involved in ion-pairing in solution, and nearly all counter-ions are involved in ion-pairing in the adsorbed state on the hydrophobic chromatography matrix. The same ion-pairing agent(s) for displacer and analyte should be used for good chromatographic resolution. Useful ion-pairing counter-ions are usually singly charged. Owing to their higher solvation energies, divalent ions ($SO_4^{2-}$, $Ca^{2+}$) and trivalent ions ($PO_4^{3-}$, $La^{3+}$) are generally less useful but may be used in some specialized cases. Exceptions to this general rule are multiple, singly-charged moieties spaced apart in a single organic ion such as $^-O_3S(CH_2)_4SO_3^-$ and $Me_3N^+(CH_2)_4N^+Me_3$.

Counter-ions with greater hydrophobic character tend to increase binding strength and also decrease solubility. Furthermore, when using hydrophobic displacer salts, resolution of DC may decrease if the counter-ion itself is either too hydrophobic or too hydrophilic. Typically, intermediate hydrophobic/hydrophilic character of the counter-ion gives best results, but this varies depending on the molecule being purified. The optimal counter-ion for each purification should be determined experimentally. For example, a hydrophobic quaternary ammonium displacer with $CH_3CO_2^-$ counter-ion gives good solubility and mediocre resolution, with $CF_3CO_2^-$ gives mediocre, but acceptable, solubility and good resolution, and with $CCl_3CO_2^-$ gives poor solubility and mediocre resolution. Volatile ion-pairing agents are conveniently removed under reduced pressure, while nonvolatile ones are readily removed by other means such as diafiltration, precipitation or crystallization. Table I gives a partial list of useful monovalent ion-pairing anions. Table II gives a partial list of useful monovalent ion-pairing cations. When using protonated-amine (pKa~9.8-11.0), protonated amidine (pKa~12.5) or protonated guanidine (pKa~13.5) ion-pairing agents, the operating pH should be 1-2 pH units or more below the pKa of the respective amine. When using anionic ion-pairing agents, the operating pH should be 1-2 pH units or more above the pKa of the respective acid. A notable exception to this guideline is trifluoroacetic acid that acts as both ion-pairing agent and pH buffer at the same time.

TABLE I

Monovalent Anions in Approximate Order of Ion-pairing Strength

| | |
|---|---|
| Weak | Fluoride < Hydroxide < Gluconate < Glycerate < Glycolate < Lactate |
| Moderate | Formate < Acetate < Bicarbonate < Propionate < Butyrate < Methanesulfonate < Ethanesulfonate < Difluoroacetate < Chloride |
| Medium Strong | Bromide < Trifluoroacetate < Dichloroacetate < Nitrate |
| Strong | Triflate < Iodide < Dibromoacetate < Thiocyanate < Trichloroacetate < Perchlorate < Hexafluoroisobutrate < Pentafluoropropionate < Tetrafluoroborate < Hexafluorophosphate < Tribromoacetate |

TABLE II

Monovalent Cations in Approximate Order of Ion-Pairing Strength $Na^+ < K^+ \sim NH_4^+ < MeNH_3^+$
$MeNH_3^+ < EtNH_3^+ < {^n}C_3H_7NH_3^+ < {^n}C_4H_9NH_3^+ < {^n}C_5H_{11}NH_3^+ < {^n}C_6H_{13}NH_3^+$
$MeC(NH_2)_2^+ < EtC(NH_2)_2^+ < {^n}C_3H_7C(NH_2)_2^+ < {^n}C_4H_9C(NH_2)_2^+ < {^n}C_5H_{11}C(NH_2)_2^+ < {^n}C_6H_{13}C(NH_2)_2^+$
$Me_2NC(NH_2)_2^+ < EtMeNC(NH_2)_2^+ < {^n}C_3H_7MeNC(NH_2)_2^+ < {^n}C_4H_9MeNC(NH_2)_2^+ < {^n}C_5H_{11}MeNC(NH_2)_2^+ < {^n}C_6H_{13}MeNC(NH_2)_2^+$ TABLE II-continued Monovalent Cations in Approximate Order of Ion-Pairing Strength $Me_2NH_2^+ < EtNMeH_2^+ < ''C_3H_7NMeH_2^+ < ''C_4H_9NMeH_2^+ <$
$''C_5H_{11}NMeH^+ < ''C_6H_{13}NMeH_2^+$
$Me_2NH_2^+ < Et_2NH_2^+ < (''C_3H_7)_2NH_2^+$
$Me_3NH^+ < EtNMe_2H^+ < ''C_3H_7NMe_2H^+ < ''C_4H_9NMe_2H^+ <$
$''C_5H_{11}NMe_2H^+ < ''C_6H_{13}NMe_2H^+$
$Me_3NH^+ < Et_2NMeH^+ < (''C_3H_7)_2NMeH^+$
$Me_3NH^+ < Et_3NH^+ < (''C_3H_7)_3NH^+$
$Me_4N^+ < EtNMe_3^+ < ''C_3H_7NMe_3^+ < ''C_4H_9NMe_3^+ < ''C_5H_{11}NMe_3^+ <$
$''C_6H_{13}NMe_3^+$
$Me_4N^+ < Me_2N^+Et_2 < Me_2N^+C_4H_8 < (''C_3H_7)_2NMe_2^+$
$Me_4N^+ < Et_3NMe^+ < (''C_3H_7)_3NMe^+$
$Me_4N^+ < Et_4N^+ < (''C_3H_7)_4N^+$ Guidelines for Estimating Ammonium-Ion-Pair Assisted Binding of Anions to RP Matrices The hydrophobicity and enhanced binding increases with the number of aliphatic carbon atoms.

For the same number of aliphatic carbon atoms, primary ammonium groups enhance analyte binding better than quaternary ammonium groups ($''Butyl-NH_3^+>Et_2NH_2^+>EtMe_2NH^+>Me_4N^+$).

For the same number of aliphatic carbon atoms, linear groups enhance analyte binding better than branched groups ($''Butyl>^iButyl$).

For the same number of aliphatic carbon atoms, linear groups enhanced analyte binding better than cyclic groups ($''Pentyl>cycloPentyl$).

For certain chemical moieties, hydrogen-binding between ammonium ions and some analytes enhance analyte binding; for example, primary ammonium to phosphate diesters (oligonucleotides) and guanidinium to carboxylates (Asp- and Glu-containing peptides).

Mixed counter-ions often lead to loss of chromatographic resolution and are generally to be avoided. However, there is one set of conditions when mixed counter-ions may be used; that is, when both (a) the counter-ion of interest has significantly stronger ion-pairing properties than the other counter-ions that are present and (b) the counter-ion of interest is present in stoichiometric excess in the sample loading mixture and in the displacer buffer.

The most commonly used ion-pairing anions are formate, acetate, chloride, bromide and trifluoroacetate. Owing to lower ion-pairing strength, formate and acetate require careful optimization in order to obtain good resolution. Bromide and trifluoroacetate seem to give the best results for peptides at low pH. Generally, good chromatographic results can be obtained with chloride and bromide as ion-pairing counter ions, but two special precautions should be exercised. (1) Under acidic conditions, the chromatography solutions cannot be degassed by helium purging or by vacuum degassing owing to loss of gaseous HCl or HBr thereby changing the pH and changing the concentration of the anion. This problem is overcome by using degassed distilled water for preparing chromatography solutions and storing the solutions in closed containers to prevent reabsorption of air. (2) Chloride and bromide are potentially corrosive to stainless steel HPLC equipmen, but equipment made from PEEK, Teflon, ceramic, glass and titanium is safe. The main problem is halide-catalyzed corrosion of stainless steel caused by air (oxygen) at low pH. If HPLC solutions are properly deoxygenated, halide-promoted corrosion of stainless steel is greatly reduced.

In order to simplify the potentially time-consuming screening of ion-pairing agents, the following recommendations serve as initial starting points for various analytes:

Peptides and small proteins (pH=2.0-3.5): $Br^-$, $CF_3CO_2^-$

Peptides and small proteins (pH=6.5-8.0): $Me_4N^+$, $Me_3NH^+$, $Me_3NEt^+$, $Me_2EtNH^+$ Oligonucleotides (pH=6.5-8.0): $''C_4H_9$—$NH_3^+$, $''C_5H_{11}$—$NH_3^+$, $''C_6H_{13}$—$NH_3^+$ DMT-On oligonucleotides (pH=7.0-8.0): $EtNH_3^+$, $Et_3NH^+$ Solubility—

In "hydrophobic chromatography" or, more properly, "solvophobic chromatography", where the principal solvent component is water, potential hydrophobic displacer molecules often have limited solubility. Hydrophobic molecules usually do not dissolve in water to any appreciable extent unless there are "hydrophillic groups" attached to the hydrophobic molecule, such as charged ionic-groups, hydrophillic counter-ions, polar groups or groups that function as hydrogen-bond donors or acceptors. Aromatic molecules intereact with water in a unique fashion owing to the unique manner in which the pi-electrons act as weak hydrogen-bond acceptors. Furthermore, aromatic molecules can engage in face-to-face pi-stacking in aqueous solution. These small but important effects are reflected in the higher solubility in water of benzene (9 mM) and naphthalene (200 μM) compared with cyclohexane (~10 μM) and trans-decalin (<1 μM) and in the higher solubility of phenol (960 mM) and β-naphthol (7 mM) compared with the unhydroxylated arenes. The molecular structure of a useful displacer molecule should facilitate a reasonable solubility (10-50 mM) in water or in water with low organic content yet at the same time be sufficiently hydrophobic that it binds strongly to the stationary phase. Generally, charged displacer molecules have better solubility properties than neutral ones owing to the increased solvation energies of charged species, especially counter-ions. It requires a unique balance of physical and chemical properties for neutral zwitterionic molecules to behave as good displacers. Neutral zwitterionic hydrophobic displacers display unique solubility properties. Unlike typical anionic or cationic compounds, neutral zwitterionic displacer compounds often increase in solubility in water as salt concentration increases. This unusual "salting-in" effect allows neutral zwitterionic compounds to be used as displacers in HIC chromatography. Furthermore, small amounts of ethanol in the aqueous displacer buffer can significantly increase solubility while similar amounts of acetonitrile have little effect.

It is important to note, generally speaking, that increasing the levels of the organic solvent in order to compensate for poor displacer solubility rarely leads to useful results. Best chromatographic results are obtained with 0-25% organic solvent, or more preferably, 2-15% organic solvent. Higher organic content (25-75%) of the mobile phase may be used in some cases but often capacity and resolution suffer badly.

Reduced Product-Displacer Association—

One problem that can arise with hydrophobic displacement chromatography is the association of a hydrophobic displacer with a hydrophobic analyte in solution. This can lead to significant loss of resolution and contamination. Displacer-analyte association in the adsorbed state on the stationary phase also can occur but is less problematic with proper amounts of ion-pairing agents present. A good method to deal with this problem is to use charged analytes and charged hydrophobic displacers with the same charge. These problems can sometimes arise when neutral hydrophobic displacers and neutral hydrophobic analytes interact, but this problem is less common when the neutral displacer has zwitterionic properties.

Displacer Self-Association and Micelle Formation—

In some cases when the chemical structure and physical properties are conducive, neutral zwitterionic hydrophobic molecules can self-associate, forming micelles and micelle-like, self-associated structures in solution. This situation can lead to loss of resolution in DC as well as unwanted foaming of displacer solutions. The displacer in solution finds itself in various forms that are interrelated by various chemical equilibria. Furthermore, micelles can act as carriers for hydrophobic analyte molecules causing them to exist in solution in various forms. This unwanted phenomenon is concentration dependent and is effectively inhibited by the addition of small amounts of a suitable organic solvent such as methanol, ethanol or acetonitrile. Properly designed, neutral zwitterionic displacer molecules disenhance micelle formation and give better displacement results. The neutral zwitterionic displacer molecules described here are far less prone to form self-associated structures in solution that neutral non-zwitterionic displacer molecules. Thus, keeping the group-hydrophobic-indices below 12.0 for R-groups, $R^1$-$R^3$, reduces the problem of unwanted detergency.

High Purity Impurities in Displacers—

A displacer should be used at an adequate degree of purity. The object of preparative chromatography is to remove the impurities from a component of interest. Contamination of the desired compound by impurities associated with the displacer itself is rarely a problem, but contamination by "early displacing" impurities in the displacer solution may be problematic in some cases depending on the amounts of the impurities and their binding properties. Thus, a good displacer should contain little or no early displacing impurities.

Suitable UV Absorbance—

In order to track the location and amounts of displacer throughout the DC experiment, to watch displacer breakthrough curves and to follow displacer removal during column regeneration procedures, it is useful to have a displacer with moderate ultraviolet absorption. High absorption is neither needed nor preferred owing to the high concentrations of displacer and analyte. Generally, colorless displacers are preferred with a UV spectrum that has strategically located windows of low absorbance corresponding to regions of UV absorbance of the analytes, so that the analytes can be followed at some frequencies and the displacer monitored at other frequencies.

Ease of Manufacturing and Cost—

Convenient and cost-effective methods of chemical synthesis, production and manufacturing are important in order to produce useful displacers and reasonable costs. Furthermore, practical methods of purification, especially non-chromatographic purification, are needed in order to achieve the purity requirements in a cost-effective manner.

Chemical Stability, Low Toxicity and Long Shelf-Life—

Among all its other desired chemical and physical properties, a useful displacer molecule should be chemically stable. It should be inert toward analyte molecules and chemically stable (non-reactive) toward water, common organic solvents, mild bases, mild acids and oxygen (air). It should be photo-stable and thermally stable under typical use and storage conditions and have a reasonable shelf-life. It is preferred that displacer molecules be visually colorless, yet have the requisite levels of UV absorbance. Dyes generally do not make useful displacers for hydrophobic displacement chromatography. Useful displacer molecules also need to have low toxicity, not only to protect workers but to protect biological and drug samples that may come into contact with the displacer.

Suitable Chromatographic Columns:

While the most common type of reversed-phase column is octadecyl coated silica, many hydrophobic stationary phases find utility in DC. Examples of suitable stationary phases are listed in Table III. Ultimately, the best choice of stationary phase is experimentally determined for each system under study.

TABLE III

Materials for Hydrophobic Stationary Phases

Coated Porous Silica (covanently bonded silanes)

| | |
|---|---|
| Octadecyl ($C_{18}$) | Docecyl ($C_{12}$) |
| Octyl ($C_8$) | Hexyl ($C_6$) |
| Butyl ($C_4$) | Pentafluorophenylpropyl ($C_6F_5$—$C_3$) |
| Phenylpropyl (Ph-$C_3$) | Phenylhexyl (Ph-$C_6$) |
| p-Biphenyl (Ph-Ph) | β-Naphthylethyl (Nap-$C_2$) |

Uncoated Porous Polystyrene/Divinylbenzene
Porous Fluorocarbon Polymer
Porous Polyoctadecylmethacrylate Polymer Carbon-like Phases:

Porous Graphitized Carbon
Cleaned Charcoal
Carbon over Porous Zirconia
$C_{18}$ Bonded to Carbon over Porous Zircona
Organic Polymer Coatings over Inorganic Oxides Mixed-Mode Hydrophobic Phases $C_{18}$ with negative surface charge
$C_{18}$ with positive surface charge
$C_{18}$ with buried negative charge
$C_{18}$ with buried positive charge Better results in displacement chromatography are obtained with longer, well-packed columns that give better recovery and yield. Table IV provides a guide for initial choices of column dimension and initial flow-rates.

TABLE IV

Chromatography Column Dimensions

| Particle Size (μm) | Column Length (mm) | Column Dia. (mm) | Column Volume (mL) | Initial Flow Rate[b] | Sample Injection Method |
|---|---|---|---|---|---|
| 2 | 100 | 2.1 | 0.3464 | 43.3 μL/min | 3 mL loop |
| 3 | 150 | 2.1 | 0.5195 | 43.3 μL/min | 5 mL loop |
| 3 | 150 | 3.0 | 1.060 | 88.4 μL/min | 10 mL loop |
| 3 | 150 | 4.6 | 2.493 | 208 μL/min | 20 mL loop/Inj. Pump |
| 5 | 250 | 4.6 | 4.155 | 208 μL/min | 40 mL loop/Inj. Pump |
| 5 | 250 | 10.0 | 19.63 | 982 μL/min | Inject. Pump |
| 5 | 250 | 20.0 | 78.54 | 3.93 mL/min | Inject. Pump |
| 10 | 500[a] | 10.0 | 39.27 | 982 μL/min | Inject. Pump |
| 10 | 500[a] | 20.0 | 157.1 | 3.93 mL/min | Inject. Pump |
| 10 | 500[a] | 30.0 | 353.4 | 8.84 mL/min | Inject. Pump |
| 10 | 500[a] | 50.0 | 981.7 | 24.5 mL/min | Inject. Pump |

[a]500 mm or 2 × 250 mm
[b]Initial flow-rate = 75 cm/hr (12.5 mm/min); needs to be optimized Proper column length is important for good results. It should be long enough to fully sharpen the displacement train and give good resolution. Yet columns that are too long needlessly increase separation time and may have poorly packed beds and reduced resolution. In many cases, two well-packed shorter columns can be attached end-to-end with good chromatographic results. Considerable experimentation with small molecules (MW<3 KDa) indicates that optimal column length falls in the range 15-45 cm for 5 μm particles and 20-60 cm for 10 μm particles. Porous particles with pore sizes of 80-100 Å are suitable for traditional drugs and small peptides, pore sizes of 120-150 Å are suitable for medium and large oligopeptides and oligonucleotides and pore sizes of 300-500 Å are suitable for most proteins and DNA. Non-porous particles can be used, but loading capacity will significantly decrease.

In cylindrical columns, it is important that a planar flow-front be established so that it is perpendicular to the axis of flow. Scaling up to purify larger amounts of sample is simple and straightforward in displacement chromatography once an optimized protocol has been developed on a smaller column. After the shortest acceptable column length is found, scale-up is simply accomplished by increasing column diameter while maintaining a constant linear flow-rate. With proper modifications, displacement chromatography can be used with radial-flow columns and with axial-flow monolith columns. The principles of displacement chromatography also can be applied in analytical and preparative thin-layer chromatography.

Running Successful Displacement Chromatography Experiments

Though displacement chromatography of organic compounds, traditional drugs and peptides has been carried out for many years, mediocre-to-poor results are often obtained. Good displacers, good columns and good operational protocols, ad dislcosed herein, lead to excellent reproduciblity and remarkably good chromatographic performance.

Displacer and Concentration—

Initial evaluation is carried out using a good general purpose neutral zwitterionic displacer with proper binding strength. Neutral zwitterionic displacers can be used to purify cationic, neutral non-ionic, neutral zwitterionic and anionic analytes. The displacer should bind to the column more strongly than the material to be purified, but the displacer should not bind too strongly. Typical displacer concentrations are in the range 10-50 mM. Initially, displacer concentration is set at 10-15 mM. As needed, pH buffer and ion-pairing agent are added to the displacer solution. The displacer solution and carrier solution should have identical compositions (including pH), except for the presence of displacer and the concentration of the ion-pairing salt. Displacers 713, 738 and 753 (see Table V, below) are examples of good general-purpose neutral zwitterionic displacers. During method optimization, it may be helpful to increase displacer concentration up to 20-30 mM or higher.

Choosing an Ion-Pairing Agent—

Not using an ion-pairing agent, using an ineffective ion-pairing agent, using mixed ion-pairing agents and using insufficient levels of a good ion-pairing agent are some of the major causes of poor chromatographic performance in displacement chromatography experiments. Tables I and II contain lists of useful, monovalent, ion-pairing anions and ion-pairing cations that are useful for hydrophobic chromatography. They are needed when the analyte or displacer is charged. For charged analytes and displacers, binding isotherms strongly depend on the chemical properties of the counter-ion and its concentration. Our data have also shown that ion-pairing salts with neutral zwitterionic displacers lead to sharper displacement bands with enhanced binding to hydrophobic stationary phases. Those ion-pairing agents with moderate to moderately strong binding properties are usually the best to use. When starting experimentation with ion-pairing agents, try bromide or trifluoroacetate (free acid or $NH_4^+$ salt) as ion-pairing anions and try $K^+$, $NH_4^+$ or protonated mono-, di- or trimethylamine (free amine or formate salt) for ion-pairing cations. Start with methylammonium trifluoroacetate ($[MeNH_3][CF_3CO_2]$) during initial experiments. When the analyte requires an ion-pairing agent, it usually dictates the choice of IP agent during the DC experiment. The ion-pairing agent (salt) for the analyte and the displacer should be the same.

Concentration of Ion-Pairing Agent—

As noted earlier, using insufficient levels of a good ion-pairing agent is one of the major causes of poor chromatographic performance in displacement chromatography experiments. The formula for calculating the suitable concentration of the ion-pairing agent in the sample solution ($C_{IPS}$, mM)) is given by, $$C_{IPS} = E_s \times C_s(mM) \times G_s$$

where $E_s$ is the excess factor for the sample, $C_s$ is the concentration of the sample (mM) and $G_s$ is the absolute value of the net charge of the sample at the operative pH. The optimal value of $E_s$ is a parameter that needs to be determined experimentally. The formula for calculating the suitable concentration of the ion-pairing agent in the displacer solution ($C_{IPD}$, mM) is given by, $$C_{IPD} = E_d \times C_d(mM) \times G_d$$

where $E_d$ is the excess factor for the displacer, $C_d$ is the concentration of the displacer (mM) and $G_d$ is the absolute value of the net charge of the displacer at the operative pH. The optimal value of $E_d$ is a parameter that needs to be determined experimentally. It is essential that at least a stoichiometric amount of the ion-pairing agent be present in the solutions ($E_s \geq 1.0$ and $E_d \geq 1.0$). In practice, it is our experience that $E_s$ should be in the range 1.1-10.0, more preferably in the range 1.2-6.0, more preferably yet in the range 1.5-4.5. Furthermore, it is our experience that $E_d$ should be in the range 1.1-10.0, more preferably in the range 1.2-4.0. Serious deterioration in chromatographic performance results when the ion-pairing concentrations are unoptimized or too low, that is $E_s < 1.0$ and/or $E_d < 1.0$.

In the case of a peptide or protein that is near its isoelectric point or of a neutral zwitterionic displacer, $G_s$ and $G_d$ are near zero. Nonetheless, we find that ion-pairing salts (ion-pairing cation with ion-pairing anion) at certain useful concentrations significantly enhance the sharpness of displacement bands of peptides/proteins (pH~pI) and of neutral zwitterionic displacers thereby leading to better displacement purifications.

In Example 2 below, better results are obtained with an ion-pairing salt than without. The peptide at pH 6.0 has two 1+ charges and two 1− charges with a net charge near zero. The displacer at pH=6.0 has one 1+ charge and one 1− charge with a net charge near zero. Good chromatographic results are obtained by assuming $G_s$ to be 2 and $G_d$ to be 1.

Choosing a RP Column—

For initial reversed-phase work, several good quality octadecyl on silica or phenylhexyl on silica columns should be evaluated (5 μm spherical particles with dimensions 4.6×250 mm). Scaleup to larger preparative columns can come later and is relatively straightforward. A critical issue is to choose a suitable pore size. Matrices with pores that are too large or too small often lead to reduced capacity and sometimes reduced resolution. See Tables III and IV above.

Flow-Rate—

Because displacement chromatography is a "quasi-equilibrium technique", relatively slow flow-rates are often needed. The optimal flow-rate is the fastest flow-rate possible without losing resolution. Sample loading flow-rate and displacement flow-rate should be about the same, both in the range of 35-105 cm/hr. Start at 75 cm/hr for traditional drugs, oligopeptides and oligonucleotides or 40 cm/hr for proteins and DNA. Regeneration flow-rates should be 2-8 times the displacement flow-rate. When purifying drugs, peptides or oligonucleotides at elevated temperatures on reversed-phase columns, even faster flow-rates can be used.

Temperature—

Because reversed-phase chromatography and other forms of hydrophobic chromatography are largely driven by $+T\Delta S$ with $+\Delta H$, higher temperature often leads to stronger binding, faster binding kinetics and distinctly different resolution. As a consequence, the temperature of the column and, to some extent, displacement buffers should be carefully regulated (+/−0.5° C.) in order to prevent band broadening. Initial work is often carried out at 25° C., and then elevated temperatures (45, 65° C.) are tried if the sample will tolerate it, and the boiling point of the organic solvent is suitable.

Choosing an Organic Solvent—

Although most water-miscible organic solvents will function, acetonitrile, methanol and ethanol are most commonly used. Some DC purifications are carried out with little or no organic solvent at all. This allows practical RPC and HIC purification of undenatured proteins with low salt and low organic solvent. Operating without organic solvent may also be helpful when there are safety issues associated with volatile, flammable solvents. When experimenting, first try acetonitrile for peptides, low molecular-weight organic drugs and small proteins or methanol for large proteins oligonucleotides and DNA. If solubility of the sample in water is acceptable, start with 3% v/v MeCN, 4% v/v EtOH or 5% v/v MeOH in the carrier buffer, the displacer buffer and sample loading solution; the organic content of these three solutions should be the same. Organic solvent content is an important parameter that needs to be optimized for each sample, column and displacer. For general purpose operation, organic solvent should be less than about 15 volume %, more preferably less than about 10 volume %, more preferably yet about 5 volume %. When Octadecyl columns are used, 2-3 volume % acetonitrile, 3-4 volume % ethanol or 4-5 volume % methanol is usually needed for optimal functioning of the matrix. Phenylhexyl and Octyl columns can usually tolerate the absence of organic solvent.

Choice of pH and pH Buffer— pH buffers are needed when there are ionizable protons in the sample, displacer, ion-pairing agent or on the stationary phase. Some samples are only stable within certain pH ranges. For some samples, chromatographic resolution is strongly pH-dependent. Generally, cationic samples are purified using neutral zwitterionic displacers and cationic buffers. The anions associated with the cationic buffers should be the same as the ion-pairing anion. In some cases, a different anion can be used as long as it has significantly weaker ion-pairing properties. Likewise, an anionic pH-buffer may be used if it has much weaker ion-pairing properties than the principle ion-pairing anion; thus, formic acid or acetic acid can be used as pH buffers when trifluoroacetate is the ion-pairing anion. For obvious reasons, neutral and cationic amines with low $pK_a$ values are useful pH-buffers: N,N,N',N'-tetramethylethylenediamine (5.9, TMEDA), N,N-dimethypiperazine (4.2, DMP), diazobicyclooctane (3.0, DABCO).

Similarly, anionic samples are purified using neutral zwitterionic displacers and anionic pH buffers. The cations associated with the anionic pH buffers should be the same as the ion-pairing cation but may be, in some cases, a cation that has significantly weaker ion-pairing properties. Furthermore, sometimes cationic pH-buffers can be used but only when they possess weaker ion-pairing properties than the principle ion-pairing cation; thus, N-methylmorpholine (7.4, NMM), triethanolamine (7.8, TEOA) and TRIS (8.1) can sometimes be used as pH buffers when trimethylammonium or triethylammonium is the ion-pairing cation. Anionic compounds with mid-range $pK_a$ values can be useful pH-buffers: TAPS (8.4), TAPSO (7.6), methylphosphonic acid (7.6, MPA), MOPS (7.2), MOPSO (6.9), phosphoric acid (6.8), monomethylphosphiric acid (6.3), phosphorous acid (6.3), MES (6.2), 3,3-dimethylglutaric acid (5.9, DMG), succinic acid (5.2, SUC), acetic acid (4.6, HOAc).

Co-Displacement—

When working with samples that contain hundreds components and impurities, co-displacement is an almost unavoidable phenomenon because there are likely to be several minor components that co-displace with the major component of interest no matter where on the binding isotherms the DC experiments take place. Fortunately, co-displacement in displacement chromatography is a far less serious problem than co-elution in preparative elution chromatography. Co-displacement occurs under two, conditions: (1) when binding isotherms are so similar that there is poor resolution and (2) when there is crossing of binding isotherms near the operating region of the binding isotherm. Fortunately, there are simple ways to deal with this issue: carry out a second DC experiment under different conditions by operating at a different point on the binding isotherms by, a. changing the concentration of the displacer,
    b. changing to a different displacer with different binding properties. Alternatively, the isotherms themselves can be changed by,
    c. changing the chromatography matrix (stationary phase),
    d. changing the concentration of the organic solvent,
    e. changing to a different organic solvent,
    f. changing to a different ion-pairing agent,
    g. changing the temperature.

A second "orthogonal" IP-RP DC step typically gives excellent purity (~99.5%) with excellent yield (90-95%).

Method of Sample Loading—

A sample is loaded onto the column through a sample injection valve using one of two methods. The sample should be loaded under frontal chromatography conditions at the same point on the binding isotherm at which the DC experiment takes place. The carrier is not passed through the column after the sample is loaded. Method 1: A sample loading pump is used; Method 2: An injection loop is used. Usually, only partial loop injection is used. The sample in the loop should be driven out of the loop onto the column first by the carrier and then the displacer solution. Not more that 85-95% of the loop volume should be loaded onto the column so that sample diluted by carrier is not loaded.

Column Loading—

DC experiments are carried out at relatively high loading, typically in the range 60-80% of maximum loading capacity. The operative column loading capacity is not a fixed number; rather, it depends upon where on the binding isotherm the DC experiment operates.

Not all of the column capacity is available for use (see "Exception" below). In practice, only 90-98% of the column capacity is usable. Once the sample has been loaded onto the column, the displacer buffer is then pumped onto the column. There are three fronts that develop, each traveling at different velocities down the column: (1) the liquid front ($T_1$, displacer buffer minus displacer), (2) the sample front ($T_2$) and (3) the displacer saturation front itself ($T_3$). The first front travels faster than the second and third fronts and limits the useable column capacity because the first front should exit the column before the displacement train ($T_2$) begins to exit. The actual velocities of the fronts depend directly on the displacement flow-rate. The ratio, $\alpha$, of the front velocities, $Vel_1/Vel_2$, is given by the formula, $$\alpha = K_m/(R \times C_d)$$

where $K_m$ is the displacer binding capacity of the matrix (mg displacer per mL packed matrix) at displacer concentration of $C_d$, where $C_d$ is the displacer concentration in the displacer buffer (mg displacer per mL displacer buffer), R is the ratio of the volume of the liquid in the column to the total volume of the column (mL liquid per mL bed volume). The maximum % usable column capacity is given by:

$$(100 \times (\alpha-1))/\alpha.$$

In Example 2 below, the respective α-value is 21.98, and the respective maximum usable capacity is 95.4%. Note that as $C_d$ increases, $K_m$ will also increase, but not as much if operating high on the nonlinear part of the isotherm. Thus, α will decrease and maximum % usable column capacity will decrease.

There is an exception to the foregoing. If significant levels of unwanted, early-displacing impurities are present in the sample, one can increase the usable capacity of the column, even beyond 100% by overloading the column and spilling out these impurities during sample loading before the displacer flow is started. Thus, the column loading could be 105% of maximum based on the whole sample, but the column loading would be only 80% based on the amount of main product plus late-displacing impurities.

Concentration and Volume of Sample Solution—

The concentration of the load sample is an important operating parameter. The optimal sample loading concentration (mg/mL) is the same as the output concentration of the purified product from the displacement experiment—the plateau region of the displacement train. Binding isotherms, the column binding capacities and the output concentrations are initially unknown. Simply carry out the first displacement experiment with the sample solution loaded onto the column using initial estimates as shown below:

(1) Pick an initial column loading percentage at which the one wishes to work, say 75%.

Sample loading time=displacer breakthrough time
$(T_3-T_1) \times 0.75 = (434 \text{ min} - 220 \text{ min}) \times 0.75 = 161$ min (for Example 2 below)

(2) Pick an initial concentration for the sample by one of two methods:

(a) Initial sample conc. (mg/mL)=0.25×disp. conc. (mM)× formula wt. (mg/μmole)=0.25×10 mM×1.7466 mg/μmole=4.37 mg/mL (for Example 2 below)

(b) Pick an estimated column binding capacity for the sample, say 50 mg sample/mL matrix. Assume displacement flow-rate and sample loading flow-rate are the same:

Initial sample conc. (mg/mL)=(col. binding capacity $(mg/mL_m) \times$ col. volume $(mL_m)/((T_2-T_1) \times$ sample flow-rate (mL/min))=(50 mg/mL$_m \times$4.155 mL$_m$)/ ((434 min−220 min)×0.208 mL/min)=4.67 mg/mL (for Example 2 below).

If the first DC experiment with loaded sample leads to overloaded conditions (>100% loading), rerun the experiment at one-half the sample concentration. From the results of the first successful DC experiment while using a sample, actual loading concentration and actual column loading capacity are readily calculated, and those values are then used in adjusting sample concentration and loading for the second DC experiment.

Sample Preparation—

The loading sample solution is prepared at the concentration and amount described above. Enough excess solution is needed for overfilling the loop or filling the dead volume of a sample loading pump and delivery lines. The pH, amount of pH buffer and amount of organic solvent are the same as the carrier and displacer buffer. Dissolving the sample in the carrier changes its pH, so the pH of the sample solution will have to be re-adjusted after dissolution. However, the amount of ion-pairing agent may be different. The ion-pairing agent used in the sample solution must be the same one used in the displacer buffer. In this regard, the ion-pairing requirements of the sample dictate which ion-pairing agent is used in the sample solution and in the displacer solution. Based on the formal chemical charge at the operating pH and the concentration of the main analyte, the concentration of the concentration is the ion-pairing agent or ion-pairing salt is calculated. See "Concentration of Ion-Pairing Agent" above.

The composition and history of the sample should be known. If the sample contains an anion or a cation, its chemical nature and amount (concentration) should also be known. (a) Obviously, if no anion or cation is present, then no adjustment is made in sample preparation. (b) If the anion/cation in the sample is the same as the ion-pairing agent used in the DC, then the amount of added ion-pairing agent to the sample solution is reduced accordingly. (c) If the anion/cation in the sample has significantly weaker ion-pairing properties than the ion-pairing agent used in the DC, then its presence is ignored. (d) If the anion/cation in the sample has stronger ion-pairing properties than the ion-pairing agent used in the DC, then the anion/cation should be exchanged or removed before proceeding.

Collecting Fractions—

Displacement chromatography gives excellent chromatographic resolution, especially with optimized protocols using a good $C_{18}$— reversed-phase column. However, the resolution is difficult to see because all of the bands come off the column together as back-to-back bands in the displacement train. Many of the small impurity triangle-bands are less than 30 seconds wide (<100 μL). Thus, an experiment with a displacer breakthrough time of 250 minutes and 80% sample loading, the displacement train would be about 200 minutes wide, and more that 400 fractions would have to be taken so that chromatographic resolution is not lost during the fraction-collection process. Analyzing 400 fractions is truly enlightening and interesting but also a daunting task. This is when online real-time fraction analysis would be useful. In practice, one may somewhat disregard resolution and collect only 100-130 larger fractions. Analysis of even this number of fractions represents a substantial amount of work.

In the circumstance in which a preparative DC experiment is conducted and only the purified main component is of interest, the fraction collecting process is greatly simplified. Based on the shape of the displacement train observed at various frequencies (UV), the beginning and ending of main band of interest is judged and then about 10 fractions are analyzed in both regions in order to determine which fractions to pool. Analyzing 20 fractions instead of 100-130 fractions is an easier task.

In Example 2 below, analysis is even easier. Based on the method above, the beginning and ending of the main band of interest is judged, a conservative pooling is made without any analysis and only one analysis is carried out on the final pool.

Displacer Removal and Column Regeneration—

The displacer is removed using 5-10 column volumes of 95/5 (v/v) ethanol-water or 80/10/10 (v/v/v) acetonitrile-$n$propanol-water without any pH buffer or ion-pairing agent. The object is to efficiently remove >99.9% or more of the displacer from the column in the shortest amount of time. The flow-rate is increased (100-400 cm/hr) in order to speed up the column regeneration process if the matrix will tolerate the increased back-pressure. Observing the displacer removal near the absorption maximum of the displacer (see displacer instructions) allows the regeneration process to be carefully monitored and optimized by UV detection.

Effects of Added Salt—

Salts in aqueous solvents lead to solvents that are less hospitable to dissolved hydrophobic analytes and hydrophobic displacers resulting in stronger binding to hydrophobic chromatographic matrices. This is the principle behind hydrophobic-interaction chromatography (HIC). So long as solubility of the analyte is sufficient in the salt solution, the addition of salt is a good way to modulate analyte binding and selectivity to a hydrophobic matrix. As noted before, neutral zwitterionic hydrophobic displacers are unique in this regard. Unlike typical anionic or cationic compounds, neutral zwitterionic displacer compounds often increase in solubility as salt concentration increases. This unusual "salting-in" effect allows neutral zwitterionic compounds to be used as displacers in HIC chromatography.

In some cases, analyte binding to a hydrophobic matrix is so weak that added salt is needed in order to obtain sufficient analyte binding. Commonly used salt solutions include one of $(NH_4)_2SO_4$, $K_2SO_4$, $Na_2SO_4$, NaCl and KCl, as a concentration of about 0.5 to about 2.5M. With the help of many different salts at various concentrations, HIC in displacement mode offers many options for useful chromatographic separations of proteins.

Instrument Protocols—

See the example protocol for Example 1 (dual pump operation). Because residual displacer from previous experiments is a potential problem, the protocol has line purging operations, a quick column regeneration and equilibration operations in order to make sure that the HPLC system and column are completely clean and properly equilibrated just before sample loading. These steps are simply precautionary and not always necessary. The protocol includes the (a) a pre-equilibration sequence, (b) an equilibration sequence, (c) a sample loading sequence (d) a displacement sequence and (e) a regeneration sequence in a single protocol. In order to overcome problems with dead-volume in the system, all loading buffers, displacer buffers and sample solutions are purged through the system to waste just prior to pumping onto the column. This way, the column sees a sharp front of undiluted solutions immediately upon valve switching. The sample solutions should be degassed so that gas bubbles do not form in them. When injection loops are used, they need to be overfilled by about 10%. The overfill can be collected for further use. Full loop injections should not be used, only partial loop injections. Experience dictates that only 85-95% of the loop volume can be used depending on the inner diameter of the loop tubing because the sample solution mixes with the driver solution and dilutes it. The sample in the loop is driven onto the column by the loading buffer, but toward the end of the sample loading process, the driving solution is changed to the displacer buffer. This allows the displacer buffer to be purged through the system just prior to the displacer buffer itself being pumped directly onto the column. During the initial part of the regeneration process, slower flow-rates are used Thus, problems with high backpressure rarely occur. Once most of the displacer has been removed, higher flow-rates can be used.

Method Optimization—

As with all forms of preparative chromatography, optimization of the chromatographic methods and procedures is important, but it requires some experimentation. The benefits of displacement chromatography often come with a price— time. The time-consuming factors can be minimized during method optimization.

Determine near optimal conditions for the displacement purification without regard for the time of the separation.

Increase the displacer concentration and the concentration of the sample loading solution until resolution decreases.

Increase the displacement flow-rate and the sample loading flow-rate until resolution decreases.

Shorten the pre-equilibration sequence and the displacer removal/column regeneration sequences.

Existing protocols provide a useful starting point for method optimization, but they will need modification for the specific sample under study. A sample protocol (Example 1) is shown below that has been optimized for purity without regard to time. It is important to carry out method optimization adapted for the specific physical properties and chromatographic properties of the sample of interest. Upon optimization, longer process times (600-800 min) often can be reduced to 200-300 minutes and in some cases reduced to 100-150 minutes.

Hydrophobic chromatography used in displacement mode has (a) high matrix productivity (gram of product per liter matrix over the lifetime of the matrix), (b) high volume productivity (gram of product per liter of column volume), (c) high solvent productivity (gram of product per liter of solvent used) yet (d) may have mediocre time productivity (gram of product per unit of time). Proper method optimization mitigates the time factor.

Properly Configured Instrumentation:

A typical instrumental configuration for a small preparative HPLC system is given below.

Main Pump: stainless steel, titanium, ceramic, PEEK; accurate 0.01-10 mL/min flow-rate; 3000-4500 psi pressure.

Optional Column Bypass Valve: two-position, six-port switching valve (stainless steel, PEEK); column inline or bypass column. This is a convenience option.

Required Sample Injection Valve: two-position, six-port injection valve (stainless steel, PEEK) for injection loop or sample injection pump.

Injection Loop: 20-40 mL injection loop (stainless steel, PEEK). Loop should be overloaded (~10%). Only partial loop injection is used, typically no more than 85-95% of loop volume. Use one, either an injection loop or a sample pump.

Sample Pump: this is similar to main pump for sample injection. Sample should be compatible with flow path of pump head. Use one, either an injection loop or a sample pump. With a two-pump operation, the flow-rates of the two pumps should be calibrated so that their flows can be matched.

No Gradient Mixer: bypass or remove the gradient mixer in displacement chromatography.

UV Detector: Multiple wavelength or photo-diode-array detector, 200-400 nm frequency range, with short-path, low-volume quartz flow-cell (0.2-2.0 mm flowpath, <10 µL flow-volume).

Optional Conductivity Detector: conductivity detector with flow cell, 0.1-200 mS, <100 µL flow-volume after UV detector; bypass conductivity flow-cell when collecting fractions for analysis at displacement flow-rate <500 µL/min.

Fraction Collector: 10 µL to 10 mL per fraction by time or by number of drops.

Column Cooler/Heater: 0-100° C.+/−0.5° C. If the column is operated at a temperature substantially different from ambient temperature, arrangements for heating or cooling the buffer solutions need to be made.

Example 1

Displacement Protocol for the Purification of Crude Synthetic α-Endorphin

Equipment Configuration:

Main Pump(1) with 4 buffer lines, Sample Loading Pump (2) with 1 solvent line, Pump Selector Valve, Column Bypass Valve Pump Selector Valve: 6-port valve controlled by single-channel toggle logic (S3=0, Pump 1 to column-Pump 2 to waste, S3=1 Pump 1 to waste-Pump 2 to column)

Column Valve: 6-port valve controlled by single-channel toggle logic (S6=0, liquid flow through column, S6=1, liquid flow bypasses column) UV photodiode array detector after column (flow-cell: 0.5 mm pathlength, 9 µL volume) followed by conductivity detector (flow-cell: 170 µL volume); conductivity flow cell is removed when fractions are being collected for analysis. Loading Buffer=A-Line on Pump 1 (S1=1, flow on, S1=0 flow off); Displacer Buffer=B-Line on Pump 1 (S2=1, flow on, S2=0 flow off); Displacer Removal Buffer=C-Line on Pump 1 (S4=1, flow on, S4=0 flow off); Column Storage Buffer=D-Line on Pump 1 (S5=1, flow on, S5=0 flow off); Sample Solution=A-line on Pump 2 (S7=1, sample flow on, S7=0 sample flow off). Sample solution is filtered (0.2µ) and degassed.

Before sequence begins, cleaned column is briefly purged with A-buffer to remove column storage buffer. See Example 2 for description of other details.

Displacer Removal Buffer (C-Buffer)=10% (v/v) 1-propanol, 10% (v/v) DI water in acetonitrile.

Column Storage Buffer (D-Buffer)=70/30 (v/v) methanol/water with formic acid (15 mM) and ammonium formate (15 mM).

Example 2

Displacement Chromatography Purification of Crude Synthetic α-Endorphin Using Displacer 740—Neutral Zwitterionic Displacer at pH 6.0, pH~pI. (see Diagram 1A)

Operating Conditions:

Starting Peptide: Desalted crude synthetic α-Endorphin (sample B), 59.3% purity, FW~1.7466 mg/µmole, charge=~0 (+2/−2) at pH=6.0.

Column: Waters Xbridge BEH130, 5 mm, 135 Å, 4.6×250 mm SS, —$C_{18}$ on silica.

Flow-Rates: Loading=208 µL/min; Displacement=208 µL/min.

Ion-Pairing Salt: Methylammonium Trifluoroacetate

Temperature=23° C. pH=6.0

Displacer Buffer: 10.0 mM Displacer 740+20 mM MES (acid)+20 mM trifluoroacetic acid in DI water w/ 5% (v/v) EtOH, pH=6.0 w/ 40% $MeNH_2$.

Loading Buffer: 20 mM MES (acid)+20 mM trifluoroacetic acid in DI water w/5% (v/v) EtOH, pH=6.0 w/ 40% $MeNH_2$.

Sample Solution: 6.88 mg/mL peptide in DI water with 5% (v/v) EtOH, 20 mM MES (acid)+20 mM trifluoroacetic acid pH=6.0 w/ 40% $MeNH_2$.

Load Amount: 226.1 mg from loading pump (pump 2); Load Time=158.0 min. (2.63 hr)

Fraction Size: 416 µL; 5 µL formic acid added to each fraction—pH reduced to 3.5; fractions are immediately frozen (−20° C.) until analysis or pooling.

| Time (min.) | Flow-Rate-1 (mL/min) | Control Switches 1234567 | Flow-Rate-2 (mL/min) | Pump 1 Operations - Functions | Pump 2 Operations - Functions | Comments | Amount |
|---|---|---|---|---|---|---|---|
| 0.00 | 0.208 | 1000001 | 0.208 | Buffer A to column | Sample to waste | Stablize System | 0.10 CV A |
| 1.98 | 0.208 | 1000011 | 0.208 | Continue | purge C-line | | |
| 2.00 | 1.039 | 0000110 | 0.000 | Buffer D to bypass | stop pump2 | Start Pre-Equilibration | 0.25 CV D |
| 3.00 | 1.039 | 1000010 | 0.000 | Buffer A to bypass | | | 0.25 CV A |
| 4.00 | 1.039 | 0001010 | 0.000 | Buffer C to bypass | | | 0.25 CV C |
| 5.00 | 1.039 | 0001000 | 0.000 | Buffer C to column | | fast regenerate | 2.0 CV C |
| 13.00 | 1.039 | 1000000 | 0.000 | Buffer A to column | | fast equilibrate | 4.0 CV A |
| 29.00 | 1.039 | 1000000 | 0.000 | continue | | | |
| 29.02 | 0.208 | 1000000 | 0.000 | Buffer A to column | | Column Equilibration | 1.0 CV A |
| 43.98 | 0.208 | 1000000 | 0.000 | | continue | | |
| 44.00 | 0.208 | 1000001 | 0.208 | | Sample to waste | purge sample line | 1.04 mL |
| 49.00 | 0.208 | 1010001 | 0.208 | Buffer A to waste | Sample to column | Start Sample Load | 32.86 mL; 7.9 CV |
| 49.02 | 0.020 | 1010001 | 0.208 | set flow-rate 0.020 | | slow Buffer A to waste | 3.04 mL |
| 200.98 | 0.020 | 1010001 | 0.208 | continue | | | |
| 201.00 | 0.208 | 0110001 | 0.208 | Buffer B to waste | | purge displacer line | 1.25 mL |
| 207.00 | 0.208 | 0100001 | 0.208 | Buffer B to column | Sample to waste | Start Displacer Flow | 77.2 mL; 18.6 CV |
| 207.50 | 0.208 | 0100001 | 0.208 | | continue | | |
| 207.52 | 0.208 | 0100000 | 0.000 | | stop sample flow | shut down pump2 | |
| 578.00 | 0.208 | 0100000 | 0.000 | continue | — | | |
| 578.02 | 0.520 | 1000000 | 0.000 | Buffer A to column | — | Start Column Regen. | 0.75 CV A |
| 584.00 | 0.520 | 0000100 | 0.000 | Buffer D to column | — | | 1.5 CV D |
| 596.00 | 0.520 | 0001000 | 0.000 | Buffer C to column | — | | 0.63 CV C |
| 611.00 | 0.520 | 0001000 | 0.000 | continue | — | | |
| 611.02 | 1.039 | 0001000 | 0.000 | Buffer C to column | — | | 6.3 CV C |
| 636.00 | 1.039 | 0000100 | 0.000 | Buffer D to column | — | | 6.0 CV D |
| 659.90 | 1.039 | 0000100 | 0.000 | continue | — | | |
| 659.98 | 0.000 | 0000100 | 0.000 | stop flow | — | | |
| 660.00 | 0.000 | 0000000 | 0.000 | close all valves | — | Stop Experiment | |

Results:

Fraction Analysis: Fraction analysis is not carried out. Purified fractions are conservatively pooled based on the shape of the displacement trace.

Analyses of pooled product are carried out using analytical elution HPLC-IPRP chromatography. Fractions are monitored at 215 nm; calculations are based on area %.

Total Run Time: 6.2 hr

Output Concentration: 7.02 mg/mL

Column Loading: 73.4% of maximum capacity based on whole sample

Column Capacity: ~74.1 mg peptide/mL matrix @ 7.02 mg peptide/mL solution based on whole sample ~107 µmole displacer/mL matrix @ 15.0 µmole displacer/mL solution Purity %: 99.0%

Yield %: 74%; data based on conservative fraction-pool without fraction analysis; actual yield is likely to be higher (80-85%).

Comments:

Sample Conc./Output Conc.=0.98

IP salt in sample=2.5 times stoichiometric amount (assume $G_s=2$)

Good results are obtained with reasonable loading capacity (74.1 g/L), excellent purity and reasonable yield (99.0% purity @>74% yield) using a small "analytical-type" column in one step from crude peptide. This example is designed to show the purification of a crude synthetic peptide where pH~pI (pH=6.0) using a neutral zwitterionic displacer. Good results are obtained in its absence (data not shown), but use of an ion-pairing salt ([MeNH$_3$][CF$_3$CO$_2$]) leads to a shaper displacement train. 20 mM concentration of ion-pairing salt is based on the assumptions that $G_s=2$, $E_s=2.5$, $G_d=1$, $E_d=2.0$; see above text. Solvent containing 5 vol % EtOH gives slightly better results with 5 vol % MeCN (data not shown). The displacer displacement band and the peptide displacement bands are quite sharp. Compared with displacement results at pH=2.0 using a cationic displacer (data not shown), these results at pH=6.0 using a zwitterionic displacer give slightly higher purity (99.0% vs 98.8%) at somewhat lower loading capacity (74 g/L vs 84 g/L); yields cannot be compared.

Example 3

HPLC Analyses

Methods 3a, 3b—Reversed-Phase for Neutral Zwitterions:

Analyses were carried out using Waters Corp. (Milford, Mass.) gradient HPLC equipped with a Waters 996 PDA detector in tandem with a Dionex/ESA Biosciences (Chelmsford, Mass.) Corona Plus CAD detector and a Waters Xbridge BEH130, 5 µm, 135 Å, 4.6×250 mm SS, —C$_{18}$ on silica, reversed-phase chromatography column (Chelmsford, Mass.).

Sample Injection: 25 µL of ~1 mM sample solution in A buffer

UV detection: 208-220 nm depending on compounds to be analyzed

Flow-Rate: 1.0 mL/min.

A buffer: 5% CH$_3$CN (v/v) in HPLC-grade dist. water with 0.1% (v/v) trifluoroacetic acid.

B buffer: 5% H$_2$O (v/v) in HPLC-grade CH$_3$CN with 0.1% (v/v) trifluoroacetic acid.

Survey Gradient Method:

| 100% A | 0-2 min |
|---|---|
| 100% A to 100% B | 2-62 min |
| 100% B | 62-70 min |

Analytical Gradient Method:

| 10% B | 0-2 min |
|---|---|
| 10% B to 50% B | 2-57 min |
| 50% B to 100% B | 57-62 min |
| 100% B | 62-67 min |

Method 3c—Reversed-Phase for Long-Chain Alkyl Halides:

Same as 10a, 10b

Sample Injection: 25 µL of ~1 mM sample solution in A buffer

UV detection: 200-220 nm depending on compounds to be analyzed

Flow-Rate: 1.0 mL/min.

A buffer: 5% CH$_3$CN (v/v) in HPLC-grade distilled water with 0.1% (v/v) trifluoroacetic acid.

B buffer: 5% H$_2$O (v/v) in HPLC-grade CH$_3$CN with 0.1% (v/v) trifluoroacetic acid.

Gradient Method:

| 50% A/50% B | 0-2 min |
|---|---|
| 50% A/50% B to 100% B | 2-62 min |
| 100% B | 62-70 min |

Example 4

Preparation of N-Benzyl-N-methyloctylamine (fw=233.39)

254.5 g Freshly distilled N-methylbenzylamine (2.1 mole, fw=121.18, ~271 mL) is added to 350 mL stirring acetonitrile in a 1 L 4-neck round-bottom flask that is equipped with a heating mantle, mechanical stirrer, 250 mL addition funnel, reflux condenser and teflon-coated thermocouple. The reaction is carried out under a nitrogen atmosphere with a slow N$_2$ purge. 135.2 g Freshly distilled 1-bromooctane (0.70 mole, fw=221.19, ~121 mL) is added to the stirring mixture in a dropwise fashion at such a rate that the reaction exotherm maintains the reaction temperature in the range 55-65° C. Under these conditions, the bromooctane addition requires about 2 hours. After the entire bromodecane is added and the reaction temperature drops below 45° C., the stirring reaction mixture is heated to 80° C. for 2 hr and then allowed cool. The reaction mixture is periodically monitored by HPLC in order to ensure that the bromooctane is entirely consumed. As the reaction cools, a less dense upper layer of the product begins to form. Upon cooling as the reaction to ambient temperature, 100 mL distilled water is added portionwise to the stirring mixture in order to facilitate phase separation and prevent crystallization of amine hydrobromide. The reaction mixture is transferred to a 1 L separatory funnel and them cooled to about −20° C. for 2 hours in order to achieve full phase separation. The lower phase is discarded and the upper phase is retained in the funnel. 1.0 L 10% w/w NaOH in distilled water is added, the mixture is thoroughly mixed and then allowed to settle for about 1 hour. The phases are again separated, the upper product phase is retained, 1.0 L distilled water is added to the mixture that is through mixed. The phases are separated after about 2 hours, and the upper product phase is placed in a rotary evaporator (80° C. bath temp.) in order to remove water, acetonitrile and some residual starting amine. This procedure yields 143 g (88%) of a pale yellow viscous liquid with a purity of 96-98% (GC, HPLC). The major impurity is the starting amine (2-4%). This material is vacuum distilled (172-175° C., 1 torr) giving a 90% distillation yield of a colorless liquid (99.8% purity). This is a clean reaction that produces good quality product if the starting secondary amine and primary alkyl halide are themselves pure.

Example 5

Preparation of N-Benzyl-N-methyl-N-$^n$octylglycine Inner Salt (fw=291.43)

116.7 g Distilled N-benzyl-N-methyloctylamine (0.50 mole, fw=233.39, 132 mL) is added to a 500 mL, 4-neck round-bottom flask that is equipped with mechanical stirrer, 250 mL addition funnel, and teflon-coated thermocouple. The reaction is carried out without solvent under a nitrogen atmosphere with a slow $N_2$ purge. To the stirring amine at ambient temperature is added 84.2 g distilled bromoacetic acid, methyl ester (0.55 mole, fw=152.97, 54 mL) in a dropwise fashion over a period of about 45 minutes. There is a small, but noticeable exotherm. The initially homogeneous reaction mixture is stirred until it becomes too viscous (about 1 hour). Within 15 minutes, a viscous, lower, product layer forms. This mixture is allowed to stand at room temperature for 20 hours during which time the entire mixture turns to a yellow, viscous oily mass. The excess alkylating agent is decanted off, and the viscous oil is carefully washed several times with MTBE. The MTBE washes are discarded. The residual MTBE is removed using a rotary evaporator yielding a crude viscous yellow oil. This water-soluble, oily product is dissolved in 350 mL distilled water at room temperature yielding a clear, pale-yellow solution. At ambient temperature, 75 g of 45% aqueous KOH is added dropwise to the stirring aqueous mixture that is contained in polypropylene flask. The ester saponification occurs almost instantly at room temperature. The mixture is briefly heated to 80° C. (30 minutes) in order to assure that the reaction is complete. The solvent (water) is completely removed using a rotary evaporator producing a sticky, pale-yellow product residue. This product is taken up in a minimum amount of of isopropyl alcohol and then filtered to remove the white solid (KBr). The clear filtrate is triturated with MTBE forming a pale yellow oil. The solvent is decanted off and the oily product is washed with MTBE which is discarded. The residual MTBE in the product is removed using a rotary evaporator. The oil is dissolved in a minimum amount of absolute ethanol and then triturated with water. The water/ethanol solvent is decanted off yielding a viscous, colorless liquid. One more round of isopropanol/MTBE trituration followed by ethanol/water trituration is carried out. The product is dried in a vacuum oven overnight and cooled to room temperature forming a pure product as a solvent-free, colorless, viscous oil (117 g, 80% yield). This material is analytically pure and has limited, but sufficient solubility in distilled water. In the presence of inorganic salts (KBr, NaCl) and organic salts ([MeNH$_3$][CF$_3$CO$_2$]), the aqueous solubility increases significantly. After standing at ambient temperature, the oil slowly solidified forming a waxy, low-melting solid.

The β-alanine derivative is analogously produced from bromopropionic acid, methyl ester; the initial quaternary ammonium bromide is a white crystalline solid, but the hydrolyzed zwitterion is a viscous liquid. The reactions with propanesultone and butane sultone are carried with the amine in acetonitrile; after the reactions are completed, the solvent is removed and the workup is similar. The reactions with sodium bromoethanesulfonate are carried out in 95/5 wt % ethanol/water. Most of the $C_{11}$, $C_{10}$ and $C_9$ compounds are isolated as low melting solids. Most $C_8$ and $C_7$ compounds are isolated as viscous liquids, some of which slowly solidify.

TABLE V

| | $R^1R^2R^3R^4N$, Neutral Zwitterions | | | | CAS | Alkylating | CAS | | Form. | Ret. |
|---|---|---|---|---|---|---|---|---|---|---|
| Nu. | $R^1$ | $R^2$ | $R^3$ | $R^4$-anionic group | Amine Num. | Agent | Num. | Formula | Weight | Time |
| 710 | $R^1 + R^2 = $ilN$^w$ | | $^n$Undecyl | $^-$SO$_3$CH$_2$CH$_2$CH$_2$— | NR$^1$R$^2$R$^3$ New | Propanesultone | 1120-71-4 | $C_{22}H_{37}NO_3S$ | 395.60 | 38.3 |
| 711 | $R^1 + R^2 = $ilN$^w$ | | $^n$Decyl | $^-$SO$_3$CH$_2$CH$_2$CH$_2$— | NR$^1$R$^2$R$^3$ 752138-59-3 | Propanesultone | 1120-71-4 | $C_{21}H_{35}NO_3S$ | 381.58 | 37.4 |
| 712 | $R^1 + R^2 = $ilN$^w$ | | $^n$Decyl | $^-$CO$_2$CH$_2$— | NR$^1$R$^2$R$^3$ 500334-33-8 | BrCH$_2$CO$_2$H + base | 79-08-3 | $C_{20}H_{31}NO_2$ | 317.47 | 38.7 |
| 713 | $R^1 + R^2 = $ilN$^w$ | | $^n$Nonyl | $^-$SO$_3$CH$_2$CH$_2$CH$_2$— | NR$^1$R$^2$R$^3$ 220712-86-7 | Propanesultone | 1120-71-4 | $C_{20}H_{33}NO_3S$ | 367.55 | 33.4 |
| 714 | $R^1 + R^2 = $ilN$^w$ | | $^n$Octyl | $^-$SO$_3$CH$_2$CH$_2$CH$_2$— | NR$^1$R$^2$R$^3$ 1197914-61-6 | Propanesultone | 1120-71-4 | $C_{19}H_{31}NO_3S$ | 353.52 | 29.4 |
| 715 | $R^1 + R^2 = $ilN$^w$ | | $^n$Octyl | $^-$SO$_3$CH$_2$CH$_2$CH$_2$CH$_2$— | NR$^1$R$^2$R$^3$ 1197914-61-6 | Butanesultone | 1633-83-6 | $C_{20}H_{33}NO_3S$ | 367.55 | 30.5 |
| 716 | $R^1 + R^2 = $ilN$^w$ | | $^n$Heptyl | $^-$SO$_3$CH$_2$CH$_2$CH$_2$— | NR$^1$R$^2$R$^3$ 1197914-59-2 | Propanesultone | 1120-71-4 | $C_{18}H_{29}NO_3S$ | 329.42 | 26.3 |
| 717 | $R^1 + R^2 = $ilN$^w$ | | $^n$Heptyl | $^-$CO$_2$CH$_2$— | NR$^1$R$^2$R$^3$ 170964-26-8 | BrCH$_2$CO$_2$H + base | 79-08-3 | $C_{17}H_{29}NO_2$ | 275.39 | 29.7 |
| 718 | $R^1 + R^2 = $ilN$^w$ | | $^n$Octyl | $^-$CO$_2$CH$_2$— | NR$^1$R$^2$R$^3$ 1197914-61-6 | BrCH$_2$CO$_2$H + base | 79-08-3 | $C_{18}H_{27}NO_2$ | 289.41 | 32.7 |
| 718b | $R^1 + R^2 = $ilN$^w$ | | $^n$Octyl | $^-$CO$_2$CH$_2$— | NR$^1$R$^2$R$^3$ 52478-47-4 | o-(BrCH$_2$)$_2$C$_6$H$_4$ + base | 91-13-4 | $C_{18}H_{27}NO_2$ | 289.41 | 32.7 |
| 719 | $R^1 + R^2 = $ilN$^w$ | | $^n$Octyl | $^-$CO$_2$CH$_2$CH$_2$— | NR$^1$R$^2$R$^3$ 119714-61-6 | Br(CH$_2$)$_2$CO$_2$H + base | 590-92-1 | $C_{19}H_{29}NO_2$ | 303.44 | 33.8 |
| 720 | $R^1 + R^2 = $ 5,6-F$_2$-ilN$^w$ | | $^n$Octyl | $^-$SO$_3$CH$_2$CH$_2$CH$_2$— | NR$^1$R$^2$R$^3$ New | Propanesultone | 1120-71-4 | $C_{19}H_{29}NO_3F_2S$ | 389.50 | 30.0 |

TABLE V-continued

| | $R^1R^2R^3R^4N$, Neutral Zwitterions | | | | Amine | CAS Num. | Alkylating Agent | CAS Num. | Formula | Form. Weight | Ret. Time |
|---|---|---|---|---|---|---|---|---|---|---|---|
| Nu. | $R^1$ | $R^2$ | $R^3$ | $R^4$-anionic group | | | | | | | |
| 721 | $R^1 + R^2 = $ THiQ$^w$ | | $n$Un-decyl | $^-SO_3CH_2CH_2CH_2$— | $NR^1R^2R^3$ | New | Propanesultone | 1120-71-4 | $C_{23}H_{39}NO_3S$ | 409.63 | 39.3 |
| 722 | $R^1 + R^2 = $ THiQ$^w$ | | $n$Decyl | $^-SO_3CH_2CH_2CH_2$— | $NR^1R^2R^3$ | 500334-33-8 | Propanesultone | 1120-71-4 | $C_{22}H_{37}NO_3S$ | 395.60 | 36.4 |
| 723 | $R^1 + R^2 = $ THiQ$^w$ | | $n$Decyl | $^-CO_2CH_2$— | $NR^1R^2R^3$ | 500334-33-8 | BrCH$_2$CO$_2$H + base | 79-08-3 | $C_{21}H_{33}NO_2$ | 331.48 | 39.7 |
| 724 | $R^1 + R^2 = $ THiQ$^w$ | | $n$Nonyl | $^-SO_3CH_2CH_2CH_2$— | $NR^1R^2R^3$ | New | Propanesultone | 1120-71-4 | $C_{21}H_{35}NO_3S$ | 381.58 | 33.4 |
| 725 | $R^1 + R^2 = $ THiQ$^w$ | | $n$Octyl | $^-SO_3CH_2CH_2CH_2$— | $NR^1R^2R^3$ | 170964-27-9 | Propanesultone | 1120-71-4 | $C_{20}H_{33}NO_3S$ | 367.55 | 30.4 |
| 726 | $R^1 + R^2 = $ THiQ$^w$ | | $n$Octyl | $^-SO_3CH_2CH_2CH_2CH_2$— | $NR^1R^2R^3$ | 170964-27-9 | Butanesultone | 1633-83-6 | $C_{21}H_{35}NO_3S$ | 381.48 | 31.5 |
| 727 | $R^1 + R^2 = $ THiQ$^w$ | | $n$Heptyl | $^-SO_3CH_2CH_2CH_2$— | $NR^1R^2R^3$ | 170964-26-8 | Propanesultone | 1120-71-4 | $C_{19}H_{31}NO_3S$ | 353.52 | 27.3 |
| 728 | $R^1 + R^2 = $ THiQ$^w$ | | $n$Heptyl | $^-CO_2CH_2$— | $NR^1R^2R^3$ | 170964-26-8 | BrCH$_2$CO$_2$H + base | 79-08-3 | $C_{18}H_{27}NO_2$ | 289.41 | 30.7 |
| 729 | $R^1 + R^2 = $ THiQ$^w$ | | $n$Octyl | $^-CO_2CH_2$— | $NR^1R^2R^3$ | 170964-27-9 | BrCH$_2$CO$_2$H + base | 79-08-3 | $C_{19}H_{29}NO_2$ | 303.44 | 33.7 |
| 730 | $R^1 + R^2 = $ THiQ$^w$ | | $n$Octyl | $^-CO_2CH_2CH_2$— | $NR^1R^2R^3$ | 170964-27-9 | Br(CH$_2$)$_2$CO$_2$H + base | 590-92-1 | $C_{20}H_{31}NO_2$ | 317.47 | 34.8 |
| 731 | $R^1 + R^2 = $(S)-THiQ-3-CO$_2$H$^w$ | | $n$Hexyl | $n$Hexyl | $HNR^1R^2$ | 74163-81-8 | 2 × $R^3$Br + 2 × base | 111-25-1 | $C_{22}H_{35}NO_2$ | 345.52 | 35.6 |
| 732 | Ph(CH$_2$)$_8$— | $R^2 + R^3 = $ —(CH$_2$)$_4$— | | $^-SO_3CH_2CH_2CH_2$— | $NR^1R^2R^3$ | New | Propanesultone | 1120-71-4 | $C_{21}H_{35}NO_3S$ | 381.58 | 31.7 |
| 733 | Ph(CH$_2$)$_8$— | $R^2 + R^3 = $ —(CH$_2$)$_4$— | | $^-CO_2CH_2$— | $NR^1R^2R^3$ | New | BrCH$_2$CO$_2$H + base | 79-08-3 | $C_{20}H_{31}NO_2$ | 317.47 | 35.0 |
| 734 | Benzyl | Meth-yl | $n$Un-decyl | $^-SO_3CH_2CH_2CH_2$— | $NR^1R^2R^3$ | New | Propanesultone | 1120-71-4 | $C_{22}H_{39}NO_3S$ | 397.62 | 38.7 |
| 735 | Benzyl | Meth-yl | $n$Decyl | $^-SO_3CH_2CH_2CH_2$— | $NR^1R^2R^3$ | 112778-25-3 | Propanesultone | 1120-71-4 | $C_{21}H_{37}NO_3S$ | 383.59 | 35.9 |
| 736 | Benzyl | Meth-yl | $n$Decyl | $^-CO_2CH_2$— | $NR^1R^2R^3$ | 500334-33-8 | BrCH$_2$CO$_2$H + base | 79-08-3 | $C_{20}H_{33}NO_2$ | 319.48 | 39.5 |
| 737 | Benzyl | Meth-yl | $n$Nonyl | $^-SO_3CH_2CH_2CH_2$— | $NR^1R^2R^3$ | 114084-69-4 | Propanesultone | 1120-71-4 | $C_{20}H_{35}NO_3S$ | 369.57 | 33.1 |
| 738 | Benzyl | Meth-yl | $n$Octyl | $^-SO_3CH_2CH_2CH_2$— | $NR^1R^2R^3$ | 63991-66-2 | Propanesultone | 1120-71-4 | $C_{19}H_{33}NO_3S$ | 355.54 | 30.2 |
| 739 | Benzyl | Meth-yl | $n$Octyl | $^-SO_3CH_2CH_2CH_2CH_2$— | $NR^1R^2R^3$ | 63991-66-2 | Butanesultone | 1633-83-6 | $C_{20}H_{35}NO_3S$ | 369.57 | 32.5 |
| 740 | Benzyl | Meth-yl | $n$Octyl | $^-CO_2CH_2$— | $NR^1R^2R^3$ | 63991-66-2 | BrCH$_2$CO$_2$H + base | 79-08-3 | $C_{18}H_{29}NO_2$ | 291.43 | 33.5 |
| 741 | Benzyl | Meth-yl | $n$Heptyl | $^-SO_3CH_2CH_2CH_2$— | $NR^1R^2R^3$ | 81404-53-7 | Propanesultone | 1120-71-4 | $C_{18}H_{31}NO_3S$ | 341.51 | 27.2 |
| 742 | Benzyl | Meth-yl | $n$Heptyl | $^-CO_2CH_2$— | $NR^1R^2R^3$ | 170964-26-8 | BrCH$_2$CO$_2$H + base | 79-08-3 | $C_{17}H_{27}NO_2$ | 277.40 | 30.5 |
| 743 | Benzyl | Meth-yl | $n$Nonyl | $^-CO_2CH_2$— | $NR^1R^2R^3$ | 114084-69-4 | BrCH$_2$CO$_2$H + base | 79-08-3 | $C_{19}H_{31}NO_2$ | 305.46 | 33.5 |
| 744 | Benzyl | Meth-yl | $n$Nonyl | $^-CO_2CH_2CH_2$— | $NR^1R^2R^3$ | 63991-66-2 | Br(CH$_2$)$_2$CO$_2$H + base | 590-92-1 | $C_{20}H_{33}NO_2$ | 319.48 | 34.6 |
| 745 | 4-FC$_6$H$_4$CH$_2$— | Meth-yl | $n$Un-decyl | $^-SO_3CH_2CH_2CH_2$— | $NR^1R^2R^3$ | New | Propanesultone | 1120-71-4 | $C_{22}H_{38}NO_3FS$ | 415.61 | 39.0 |
| 746 | 4-FC$_6$H$_4$CH$_2$— | Meth-yl | $n$Decyl | $^-SO_3CH_2CH_2CH_2$— | $NR^1R^2R^3$ | New | Propanesultone | 1120-71-4 | $C_{21}H_{36}NO_3FS$ | 401.58 | 36.2 |
| 747 | 4-FC$_6$H$_4$CH$_2$— | Meth-yl | $n$Decyl | $^-CO_2CH_2$— | $NR^1R^2R^3$ | New | BrCH$_2$CO$_2$H + base | 79-08-3 | $C_{20}H_{32}NO_2F$ | 337.47 | 39.8 |
| 748 | 4-FC$_6$H$_4$CH$_2$— | Meth-yl | $n$Nonyl | $^-SO_3CH_2CH_2CH_2$— | $NR^1R^2R^3$ | New | Propanesultone | 1120-71-4 | $C_{20}H_{34}NO_3FS$ | 387.56 | 33.4 |
| 749 | 4-FC$_6$H$_4$CH$_2$— | Meth-yl | $n$Octyl | $^-SO_3CH_2CH_2CH_2$— | $NR^1R^2R^3$ | New | Propanesultone | 1120-71-4 | $C_{19}H_{32}NO_3FS$ | 373.53 | 30.5 |
| 750 | 4-FC$_6$H$_4$CH$_2$— | Meth-yl | $n$Octyl | $^-SO_3CH_2CH_2CH_2CH_2$— | $NR^1R^2R^3$ | New | Butanesultone | 1633-83-6 | $C_{20}H_{34}NO_3FS$ | 387.56 | 32.8 |
| 751 | 4-FC$_6$H$_4$CH$_2$— | Meth-yl | $n$Octyl | $^-SO_3CH_2CH_2$— | $NR^1R^2R^3$ | New | Br(CH$_2$)$_2$SO$_3$Na | 4263-52-9 | $C_{18}H_{30}NO_3FS$ | 359.50 | 29.4 |
| 752 | 4-FC$_6$H$_4$CH$_2$— | Meth-yl | $n$Heptyl | $^-SO_3CH_2CH_2CH_2$— | $NR^1R^2R^3$ | New | Propanesultone | 1120-71-4 | $C_{18}H_{30}NO_3FS$ | 359.50 | 27.5 |
| 753 | 4-FC$_6$H$_4$CH$_2$— | Meth-yl | $n$Heptyl | $^-CO_2CH_2$— | $NR^1R^2R^3$ | New | BrCH$_2$CO$_2$H + base | 79-08-3 | $C_{17}H_{26}NO_2F$ | 295.39 | 30.8 |
| 754 | 4-FC$_6$H$_4$CH$_2$— | Meth-yl | $n$Octyl | $^-CO_2CH_2$— | $NR^1R^2R^3$ | New | BrCH$_2$CO$_2$H + base | 79-08-3 | $C_{18}H_{28}NO_2F$ | 309.42 | 33.8 |
| 755 | 4-FC$_6$H$_4$CH$_2$— | Meth-yl | $n$Octyl | $^-CO_2CH_2CH_2$— | $NR^1R^2R^3$ | New | β-propiolactone | 57-57-8 | $C_{19}H_{30}NO_2F$ | 323.45 | 34.9 |
| 755b | 4-FC$_6$H$_4$CH$_2$— | Meth-yl | $n$Octyl | $^-CO_2CH_2CH_2$— | $NR^1R^2R^3$ | New | Br(CH$_2$)$_2$CO$_2$H + base | 590-92-1 | $C_{19}H_{30}NO_2F$ | 323.45 | 34.9 |

TABLE V-continued

| | $R^1R^2R^3R^4N$, Neutral Zwitterions | | | | | CAS | Alkylating | CAS | | Form. | Ret. |
|---|---|---|---|---|---|---|---|---|---|---|---|
| Nu. | $R^1$ | $R^2$ | $R^3$ | $R^4$-anionic group | Amine | Num. | Agent | Num. | Formula | Weight | Time |
| 756 | $NR^1R^2R^3$: N-Benzyl-N'-octanoylpiperazine | | | $^-CO_2CH_2-$ | $NR^1R^2R^3$ | 289476-04-6 | $BrCH_2CO_2H$ + base | 79-08-3 | $C_{21}H_{32}N_2O_3$ | 360.49 | 35.7 |
| 757 | $NR^1R^2R^3$: 1-Benzyl-4-(caprylamido)piperidine | | | $^-CO_2CH_2-$ | $NR^1R^2R^3$ | New | $BrCH_2CO_2H$ + base | 79-08-3 | $C_{22}H_{33}N_2O_3$ | 373.51 | 36.9 | w: THiQ = 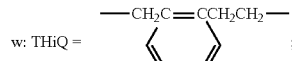 ;

iIN = 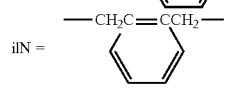

756 = 

757 = 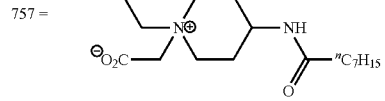

The invention claimed is:

1. A process for separating organic compounds from a mixture by reverse-phase displacement chromatography, comprising:
   providing a hydrophobic stationary phase;
   applying to the hydrophobic stationary phase a mixture comprising organic compounds to be separated;
   displacing the organic compounds from the hydrophobic stationary phase by applying thereto an aqueous composition comprising a non-surface active hydrophobic neutral zwitterionic displacer molecule; and
   collecting a plurality of fractions eluted from the hydrophobic stationary phase containing the separated organic compounds;
   wherein the non-surface active hydrophobic neutral zwitterionic displacer molecule comprises a hydrophobic neutral zwitterion having the general formula:

[CM-R*—CM']

wherein in the general formula, CM is an independent hydrophobic chemical moiety with a formal positive (+) charge selected from: quaternary ammonium (I), quaternary phosphonium (II), sulfonium (III), sulfoxonium (IV), imidazolinium (amidinium) (V), guanidinium (VI), imidazolium (VII), 1,2,3,4-tetrahydroisoquinolinium (VIII), 1,2,3,4-tetrahydroquinolinium (IX), isoindolinium (X), indolinium (XI), benzimidazolium (XII), pyridinium (XIIIa, XIIIb, XIIIc, XIIId), quinolinium (XIV), isoquinolinium (XV), and CM' is an independent hydrophobic chemical moiety with a formal negative (−) charge selected from: carboxylate (XVI), N-acyl-α-amino acid (XVII), sulfonate (XVIII), sulfate monoester (XIX), phosphate monoester (XX), phosphate diester (XXI), phosphonate monoester (XXII), phosphonate (XXIII), tetraaryl borate (XXIV), boronate (XXV), boronate ester (XXVI); wherein the chemical moieties (I)-(XXVI) have the following chemical structures:

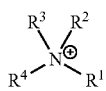   I

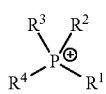   II

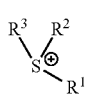   III

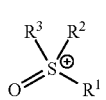   IV

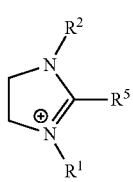   V

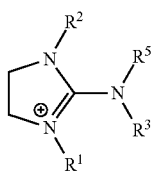   VI

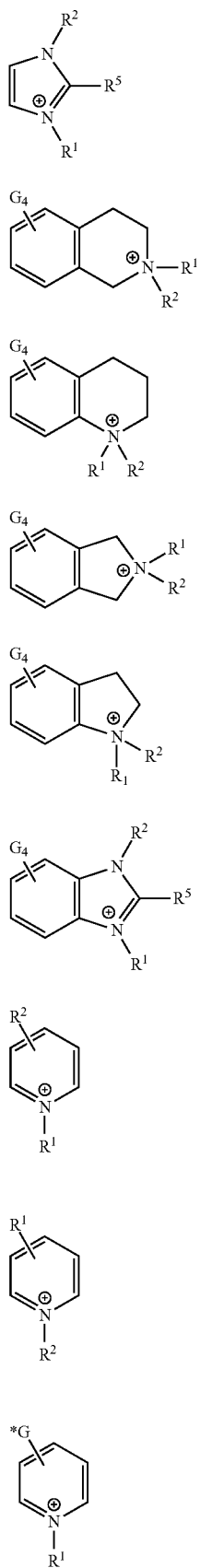
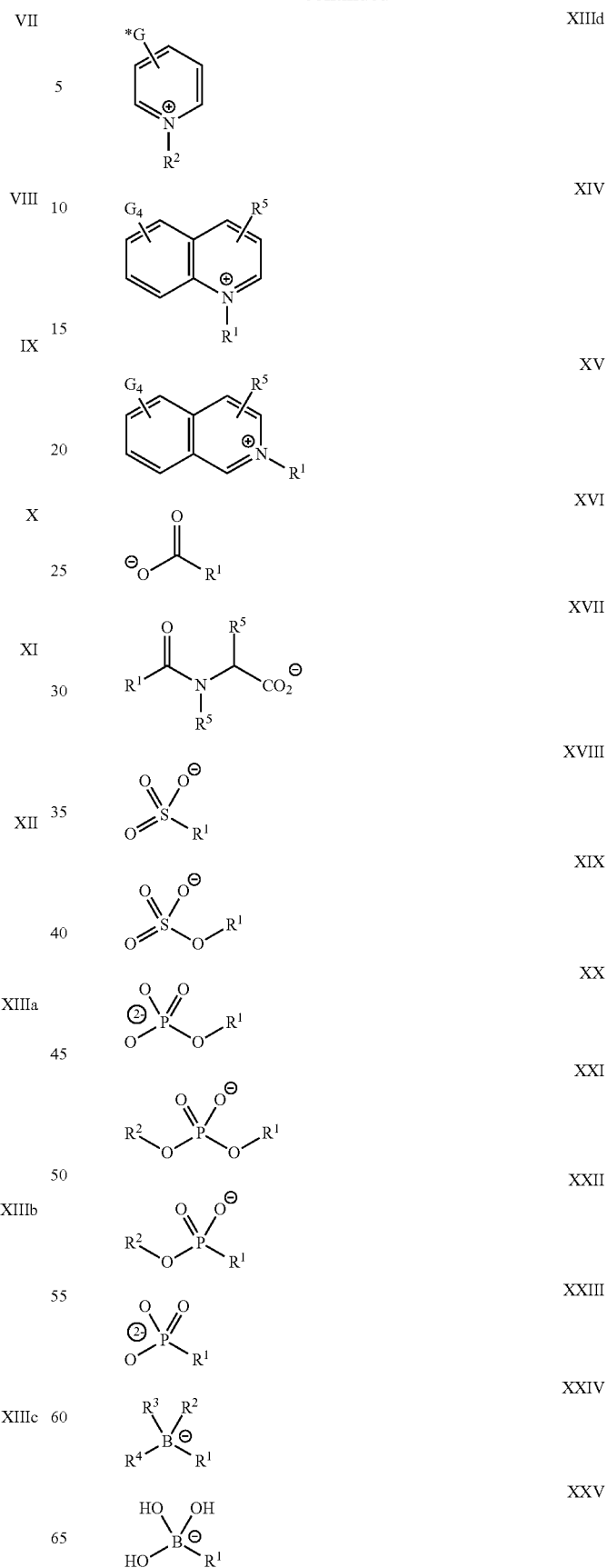

-continued

XXVI

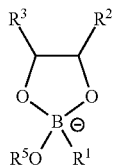

wherein in the general formula, CM and CM' are independent charged chemical moieties having the opposite formal charge such that the molecule as a whole is an electrically neutral zwitterion having zero formal charge at operational pH and CM and CM' are chemically attached to each other by a doubly connected chemical moiety, R*, which replaces one $R^1$, $R^2$(if present), $R^3$ (if present) or $R^4$ (if present) chemical moiety on CM and replaces one $R^{1'}$, $R^{2'}$ (if present), $R^{3'}$ (if present) or $R^{4'}$ (if present) chemical moiety on CM', wherein, when any $R^1$, $R^2$, $R^3$, and $R^4$ is present on CM', it is designated $R^{1'}$, $R^{2'}$, $R^{3'}$, and $R^{4'}$;

wherein each of $R^1$, $R_{1'}$, $R^2$, $R^{2'}$, $R^3$, $R^{3'}$, $R^4$ and $R^{4'}$ is a linear or branched chemical moiety independently defined by the formula, $$-C_xX_{2x-2r}-AR^1-C_uX_{2u-2s}-AR^2,$$

R* is a direct chemical bond or is a doubly connected, linear or branched chemical moiety defined by the formula, $$-C_xX_{2x-2r}-AR^1-C_uX_{2u-2s}-,$$

and $R^5$ is a linear or branched chemical moiety defined by the formula, $$-C_xX_{2x-2r}-AR^2;$$

wherein each $AR^1$ independently is a doubly connected methylene moiety ($-CX^1X^2-$, from methane), a doubly connected phenylene moiety ($-C_6G_4-$, from benzene), a doubly connected naphthylene moiety ($-C_{10}G_6-$, from naphthalene) or a doubly connected biphenylene moiety ($-C_{12}G_8-$, from biphenyl);

wherein $AR^2$ independently is hydrogen (—H), fluorine (—F), a phenyl group ($-C_6G_5$), a naphthyl group ($-C_{10}G_7$) or a biphenyl group ($-C_{12}G_9$);

wherein each X, $X^1$ and $X^2$ is individually and independently —H, —F, —Cl or —OH;

wherein any methylene moiety ($-CX^1X^2-$) within any $-C_xX_{2x-2r}-$ or within any $-C_uX_{2u-2s}-$ or within any $-(CX^1X^2)_p-$ may be individually and independently replaced with an independent ether-oxygen atom, —O—, an independent thioether-sulfur atom, —S—, or an independent ketone-carbonyl group, —C(O)—, in such a manner that each ether-oxygen atom, each thioether-sulfur atom or each ketone-carbonyl group is bonded on each side to an aliphatic carbon atom or an aromatic carbon atom;

wherein not more than two ether-oxygen atoms, not more than two thioether-sulfur atoms and not more than two ketone-carbonyl groups may be replaced into any $-C_xX_{2x-2r}-$ or into any $-C_uX_{2u-2s}-$;

wherein $m_x$, is the total number of methylene groups in each $-C_xX_{2x-2r}-$ that are replaced with ether-oxygen atoms, thioether-sulfur atoms and ketone-carbonyl groups, and $m_u$, is the total number of methylene groups in each $-C_uX_{2u-2s}-$ that are replaced with ether-oxygen atoms, thioether-sulfur atoms and ketone-carbonyl groups;

wherein G is individually and independently any combination of —H, —F, —Cl, —$CH_3$, —OH, —$OCH_3$, —$N(CH_3)_2$, —$CF_3$, —$CO_2Me$, —$CO_2NH_2$; —$CO_2NHMe$, —$CO_2NMe_2$;

wherein G* is individually and independently any combination of —F, —Cl, —$R^2$, —OH, —$OR^2$, —$NR^2R^3$, —$CF_3$, —$CO_2Me$, —$CO_2NH_2$; —$CO_2NHMe$, —$CO_2NMe_2$;

wherein a pair of $R^2$, $R^{2'}$, $R^3$, $R^{3'}$, $R^4$ and $R^{4'}$ may comprise a single chemical moiety such that $R^2/R^3$, $R^2/R^4$, $R^3/R^4$, $R^{2'}/R^{3'}$, $R^{2'}/R^{4'}$ or $R^{3'}/R^{4'}$ is individually and independently $-(CX^1X^2)_p-$ with p=3, 4, 5 or 6;

wherein the integer values of each of x, r, u, s, $m_x$, $m_u$ are independently selected for each $R^1$, $R^{1'}$, $R^2$, $R^{2'}$, $R^3$, $R^{3'}$, $R^4$, $R^{4'}$, $R^5$ and R*, integer values r and s are the total number of contained, isolated cis/trans olefinic (alkene) groups plus the total number of contained simple monocyclic structures and fall in the ranges 0≤r≤2 and 0≤s≤2, the numeric quantity $x+u-m_x-m_u$ falls in the range $0≤x+u-m_x-m_u≤11$;

wherein at least one aromatic chemical moiety, heterocyclic aromatic chemical moiety, imidazoline chemical moiety, amidine chemical moiety or guanidine chemical moiety is contained within CM or CM';

wherein a group-hydrophobic-index for each R-chemical-moiety (n) is numerically equal to the sum of the number of aliphatic carbon atoms plus the number of olefinic carbon atoms plus the number of thioether-sulfur atoms plus the number of chlorine atoms plus one-fifth the number of fluorine atoms plus one-half the number of ether-oxygen atoms plus one-half the number of ketone-carbon atoms plus one-half the number of aromatic carbon atoms beyond the number six minus the number of hydroxyl-oxygen atoms beyond the number one;

wherein an overall-hydrophobic-index (N) for each [CM-R*-CM'] is numerically equal to the sum of the number of aliphatic carbon atoms plus the number of olefinic carbon atoms plus the number of thioether-sulfur atoms plus the number of chlorine atoms plus one-fifth the number of fluorine atoms plus one-half the number of ether-oxygen atoms plus one-half the number of ketone-carbon atoms plus one-half the number of aromatic carbon atoms beyond the number six minus the number of hydroxyl-oxygen atoms beyond the number one;

wherein each of the group-hydrophobic-indices ($^1n$ and $^{1'}n$) for $R^1$ and $R^{1'}$ fall in the range $4.0<^1n, ^{1'}n<12.0$, each of the group-hydrophobic-indices ($^2n$, $^{2'}n$, $^3n$, $^{3'}n$, $^5n$, $^{5'}n$ and *n) for $R^2$, $R^{2'}$, $R^3$, $R^{3'}$, $R^5$, $R^{5'}$, R*, when present, fall in the range $0.0≤^2n, ^{2'}n, ^3n, ^{3'}n, ^5n, ^{5'}n, *n <12.0$ and each of the group-hydrophobic-indices ($^4n$ and $^{4'}n$) for $R^4$ and $R^{4'}$, when present, fall in the range $0.0≤^4n, ^{4'}n≤5.0$;

wherein the overall-hydrophobic-index (N) falls in the range 10.0≤N<24.0;

wherein the numeric value of the group-hydrophobic-index calculated for a cyclic chemical moiety is divided equally between the two respective R-chemical-moieties;

wherein $R^1$ is identified as that R-chemical-moiety when only one such chemical moiety is attached to CM or CM'; wherein $R^1$ is identified as that R-chemical-moiety having the largest value of the group-hydrophobic-index when there are more than one such chemical moieties attached to CM or CM'; wherein $R^4$ is identified as that R-chemical-moiety having the smallest value of the group-hydrophobic-index when there are more than three such chemical moieties attached to CM or CM'.

2. The process of claim 1 wherein the aqueous composition comprising a non-surface active zwitterionic hydrophobic displacer molecule is free of added salt other than a pH buffer.

3. The process of claim 1 wherein CM has a general formula I or II:

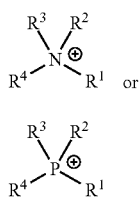

wherein in the general formula I or II, $R^1$ is a $C_8$-$C_{11}$ hydrocarbyl moiety, $R^2$ and $R^3$ are independently a $C_1$-$C_4$ hydrocarbyl moiety or benzyl, and $R^4$ is selected from benzyl, halo-substituted benzyl, 4-alkylbenzyl, 4-trifluoromethyl benzyl, 4-phenylbenzyl, 4-alkoxybenzyl, 4-acetamidobenzyl, $H_2NC(O)CH_2$-, $PhHNC(O)CH_2$-, dialkyl-$NC(O)CH_2$-, wherein alkyl is $C_1$-$C_4$, provided that no more than one benzyl group is present in the CM.

4. The process of claim 1 wherein CM has a general formula I or II:

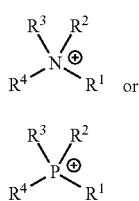

wherein in the general formula I or II, $R^1$ and $R^2$ are independently $C_4$-$C_8$ alkyl or cyclohexyl, $R^3$ is $C_1$-$C_4$ alkyl, and $R^4$ is phenyl, 2-, 3- or 4-halophenyl, benzyl, 2-, 3- or 4-halobenzyl, 2,3-, 2,4-, 2,5-, 2,6-, 3,4- or 3,5-dihalobenzyl, 2,4,6- or 3,4,5-trihalobenzyl, $C_6H_5CH_2CH_2$- or 2-, 3- or 4-trifluoromethylbenzyl.

5. The process of claim 1 wherein CM has a general formula VIII, IX, X or XI, $R^1$ is $C_5$-$C_{11}$ alkyl and $R^2$ is $C_1$-$C_8$ alkyl.

6. The process of claim 1 wherein CM has a general formula I or II:

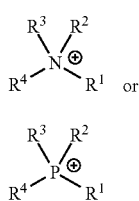

wherein in the general formula I or II, $R^1$ is $C_6$-$C_{11}$ alkyl, $R^2$ and $R^3$ independently are $C_1$-$C_4$ alkyl, and $R^4$ is $PhC(O)CH_2$-, 4-$FC_6H_4C(O)CH_2$-, 4-$CH_3C_6H_4C(O)CH_2$-, 4-$CF_3C_6H_4C(O)CH_2$-, 4-$ClC_6H_4C(O)CH_2$-, 4-$BrC_6H_4C(O)CH_2$-, dl-$PhC(O)CH(Ph)$-, $Ph(CH_2)_2$-, $Ph(CH_2)_3$-, $Ph(CH_2)_4$-, dl-$PhCH_2CH(OH)CH_2$-, t-$PhCH=CHCH_2$-, 1-$(CH_2)$naphthylene, 9-$(CH_2)$anthracene, 2-, 3- or 4-$FC_6H_4CH_2$- or benzyl.

7. The process of claim 1 wherein CM has a general formula I or II:

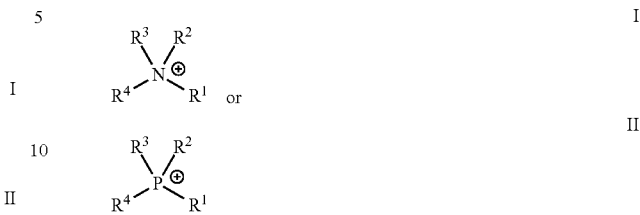

wherein in the general formula I or II, $R^1$ is $C_6$-$C_{11}$ alkyl, $R^2$ and $R^3$ together are —$(CH_2)_4$-, and $R^4$ is $PhC(O)CH_2$-, 4-$FC_6H_4C(O)CH_2$-, 4-$CH_3C_6H_4C(O)CH_2$-, 4-$CF_3C_6H_4C(O)CH_2$-, 4-$ClC_6H_4C(O)CH_2$-, 4-$BrC_6H_4C(O)CH_2$-, dl-$PhC(O)CH(Ph)$-, $Ph(CH_2)_2$-, $Ph(CH_2)_3$-, $Ph(CH_2)_4$-, dl-$PhCH_2CH(OH)CH_2$-, t-$PhCH=CHCH_2$-, 2-, 3- or 4-$FC_6H_4CH_2$-, benzyl, 3-$ClC_6H_4CH_2$-, 2,6-$F_2C_6H_3CH_2$-, 3,5-$F_2C_6H_3CH_2$-, 4-$CH_3C_6H_4CH_2$-, 4-$CH_3CH_2C_6H_4CH_2$-, 4-$CH_3OC_6H_4CH_2$-, $(CH_3)_2NC(O)CH_2$- or $(CH_3CH_2)_2NC(O)CH_2$-.

8. The process of claim 1 wherein CM has a general formula I or II:

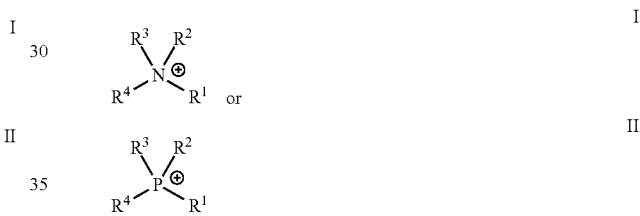

wherein in the general formula I or II, $R^1$ is $C_4$-$C_6$ alkyl, benzyl or 2-, 3- or 4-$FC_6H_4CH_2$-, $R^2$ and $R^3$ independently are $C_1$-$C_8$ alkyl, $CH_3(OCH_2CH_2)_2$-, $CH_3CH_2OCH_2CH_2OCH_2CH_2$- or $CH_3CH_2OCH_2CH_2$-, and $R^4$ is $Ph(CH_2)_4$-, 4-$PhC_6H_4CH_2$-, 4-$FC_6H_4CH_2$-, 4-$CF_3C_6H_4CH_2$-, $PhC(O)CH_2$-, 4-$FC_6H_4C(O)CH_2$-, 4-$PhC_6H_4C(O)CH_2$-, 4-$PhC_6H_4CH_2$-, naphthylene-1-$CH_2$-, anthracene-9-$CH_2$- or $Ph(CH_2)_n$-, where n=5-8.

9. The process of claim 1 wherein CM has a general formula $[(R^1R^2R^3NCH_2)_2C_6H_3G]^{2+}$, wherein $R^1$ is $C_4$-$C_{11}$ alkyl, $R^2$ and $R^3$ independently are $C_1$-$C_6$ alkyl or $R^2$ and $R^3$ taken together are —$(CH_2)_4$—, and G is H or F.

10. The process of claim 1 wherein CM has a general formula $[R^1R^2R^3NCH_2C_6H_4$-$C_6H_4CH_2NR^1R^2R^3]^{2+}$, wherein $R^1$ is $C_4$-$C_{11}$ alkyl, $R^2$ and $R^3$ independently are $C_1$-$C_6$ alkyl or $R^2$ and $R^3$ taken together are —$(CH_2)_4$—.

11. The process of claim 1 wherein CM has a general formula III or IV:

wherein in the general formula III or IV, $R^1$ is $C_8$-$C_{11}$ alkyl or 4,4'-$CH_3(CH_2)_4C_6H_4$-$C_6H_4CH_2$-, $R^2$ is $C_1$-$C_6$ alkyl or 4-$FC_6H_4CH_2$-, and $R^3$ is $C_1$-$C_6$ alkyl.

12. The process of claim 1 wherein CM has a general formula XIV or XV:

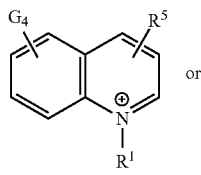

XIV

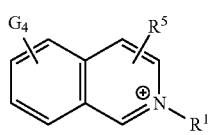

XV wherein in the general formula XIV or XV, $R^1$ is $C_8$-$C_{11}$ alkyl, and each G and $R^5$ are as defined above.

13. The process of claim 1 wherein CM has a general formula XIIIa, XIIIb, XIIIc, XIIId or XIIIe:

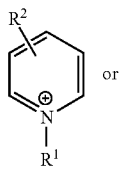

XIIIa

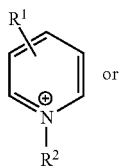

XIIIb

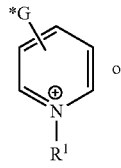

XIIIc

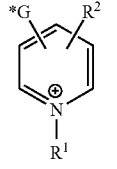

XIIId

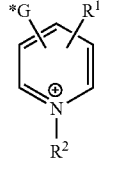

XIIIe wherein in the general formula XIIIa, XIIIb, XIIIc, XIIId or XIIIe, $R^1$ is $C_8$-$C_{11}$ alkyl or $C_8$-$C_{11}$ 4-phenyl, $R^2$ is H, $C_1$-$C_6$ alkyl or alkoxy, 2-pyridyl, $C_1$-$C_6$ alkyl substituted 2-pyridyl, or pyrrolidinyl, and each G is as defined above.

14. The process of claim 1 wherein CM has a general formula VII:

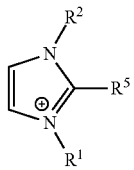

VII wherein in the general formula VII, $R^1$ is $C_5$-$C_{11}$ alkyl, $R^2$ and $R^5$ are independently H or $C_1$-$C_6$ alkyl or phenyl.

15. The process of claim 1 wherein CM has a general formula XII:

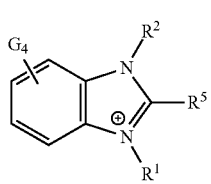

XII wherein in the general formula XII, $R^1$ is $C_5$-$C_{11}$ alkyl, $R^2$ and $R^5$ are independently H or $C_1$-$C_6$ alkyl or phenyl, and G is as defined above.

16. The process of claim 1 wherein CM' has a general formula XXIV or XXV:

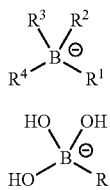

XXIV

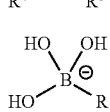

XXV wherein in the general formula XXIV, $R^1$ is phenyl, 4-$EtC_6H_4$-, 4-$^nPrC_6H_4$-, 4-$^nBuC_6H_4$-, 4-$MeOC_6H_4$-, 4-$FC_6H_4$-, 4-$MeC_6H_4$-, 4-$MeOC_6H_4$-, 4-$EtC_6H_4$-, 4-$ClC_6H_4$-, or $C_6F_5$-; and each of $R^2$, $R^3$ and $R^4$ independently are phenyl, 4-$FC_6H_4$-, 4-$MeC_6H_4$-, 4-$MeOC_6H_4$-, 4-$EtC_6H_4$-, 4-$ClC_6H_4$- or $C_6F_5$-; and wherein in the general formula XXV, $R^1$ is 4-(4-$^nBuC_6H_4$)$C_6H_4$- or 4-(4-$^nBuC_6H_4$)-3-$ClC_6H_3$-.

17. The process of claim 1 wherein CM' has a general formula selected from 4-$R^1C_6H_4SO_3H$, 5-$R^1$-2-HO-$C_6H_3SO_3H$, 4-$R^1$-$C_6H_4$-$C_6H_3X$-4'-$SO_3H$, and 4-$R^1$-$C_6H_4$-$C_6H_3X$-3'-$SO_3H$, wherein $R^1$ is $CH_3(CH_2)_n$, wherein n=4-10 and X is H or OH.

18. The process of claim 1 wherein CM' has a general formula XVIII or XXIII:

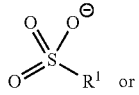

XVIII or

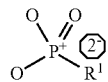

XXIII wherein in the general formula XVIII and in the general formula XXIII, $R^1$ is $C_6H_5(CH_2)_n$-, wherein n=5-11.

19. The process of claim 1 wherein CM' has a general formula selected from 5-$R^1$-2-HO-$C_6H_3CO_2H$ and $R^1C(O)NHCH(C_6H_5)CO_2H$, wherein $R^1$ is $CH_3(CH_2)_n$-, wherein n=4-10.

20. The process of claim 1 wherein CM' has a general formula 4-$R^1C_6H_4PO_3H_2$ wherein $R^1$ is $CH_3(CH_2)_n$-, wherein n=4-10.

21. The process of claim 1 wherein the aqueous composition further comprises an organic solvent, in an amount of less than about 25% by volume, or less than about 20% by volume, or less than about 15% by volume, or less than about 10% by volume, or less than about 5% by volume.

* * * * *